US006660273B2

(12) United States Patent
Pletnev et al.

(10) Patent No.: US 6,660,273 B2
(45) **Date of Patent: *Dec. 9, 2003**

(54) CHIMERIC VACCINE AGAINST TICK-BORNE ENCEPHALITIS VIRUS

(75) Inventors: Alexander Pletnev, Rockville, MD (US); Ruhe Men, Rockville, MD (US); Robert Chanock, Bethesda, MD (US); Ching-Juh Lai, Bethesda, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 10/279,130

(22) Filed: Oct. 23, 2002

(65) Prior Publication Data

US 2003/0165539 A1 Sep. 4, 2003

Related U.S. Application Data

(63) Continuation of application No. 09/518,036, filed on Mar. 3, 2000, now Pat. No. 6,497,884, which is a continuation of application No. PCT/US98/21308, filed on Oct. 8, 1998.

(60) Provisional application No. 60/061,441, filed on Oct. 8, 1997.

(51) Int. Cl.[7] ........................ A61K 39/12; A01N 63/00; C12N 15/00; C12P 21/06

(52) U.S. Cl. ................................ 424/218.1; 424/199.1; 424/93.2; 424/93.1; 435/320.1; 435/235.1; 435/69.3; 435/236; 536/23.72

(58) Field of Search ........................... 424/218.1, 199.1, 424/93.2, 93.1; 435/320.1, 235.1, 69.3, 236; 536/23.72

(56) References Cited

U.S. PATENT DOCUMENTS 6,497,884 B1 12/2002 Pletnev et al. ........... 424/218.1

OTHER PUBLICATIONS

Bancroft, et al. (1977) Identification of dengue viruses from the Caribbean by plaque–reduction neutralization test. Dengue in the Caribbean. 173–178.

Bosma, et al. (1983) A severe combined immunodeficiency mutation in the mouse. Nature. V. 301:527–530.

Bray, et al. (1991) Construction of intertypic chimeric dengue viruses by substitution of structural protein genes. Proc.Natl.Acad.Sci. V.88:10342–10346.

Cahour, et al. (1995) Growth–restricted dengue virus mutants containing deletions in the 5' noncoding region of the RNA genome. Virology 207:68–76.

Calisher, et al. (1989) Antigenic relationships between flaviviruses as determined by cross–neutralization tests with polyclonal antisera. J.Gen.Virol. 70:37–43.

Chambers, et al. (1990) Flavivirus genome organization, expression, and replication. Annu.Rev.Microbiol. 44:649–688.

Clarke, et al. (1958) Techniques forhemmagglutination and hemagglutination–inhibition with arthropod–borne viruses. Am.J.Trop.Med.Hyd. 7:561–573.

De Madrid, et al. (1974) The flaviviruses (Group B arboviruses): a cross–neutralization study. J.Gen.Virol. 23:91–96.

Dobrikova, et al. (1995) A full–size DNAcopy of the tick–borne encephalitis virus genome. Bioorg.Chem. 21:528–534.

Elroy–Stein, et al. (1989) Cap–independent translation of mRNA conferred by encephalomyocarditis virus 5' sequence improves the performance of the vaccinia virus/bacteriophage T7 hybrid expression system. Proc.Natl.Acad.Sci. 86:6126–6130.

Gentry, et al. (1982) Identification of distinct antigenic determinants on dengue–2 virus using monoclonal antibodies. Am.J.Trop.Med.Hyg. 31:548–555.

Gordon Smith (1956) A virus resembling russian spring–summer encephalitis virus from an ixodid tick in malaya. Nature. 178:581–582.

Hahn, et al. (1988) Nucleotide sequence of dengue 2 RNA and comparison of the encoded proteins with those of other flaviviruses. Virology 162:167–180.

Hambleton, et al. (1983) Pathogenesis and immune response of caccinated and unvaccinated rhesus monkeys to tick–borne encephalitis virus. Infection and Immunity. 40:995–1003.

Harabacz, et al. (1992) A randomized phase II study of a new tick–borne encephalitis vaccine using three difference doses and two immunization regimens. Vaccine. 10:145–150.

Heinz, et al. (1983) A topological and functional model of epitopes on the structural glycoprotein of tick–borne encephalitis virus defined by monoclonal antibodies. Virology. 126:525–537.

Holzmann, et al. (1990) A single amino acid substitution in envelope protein E of tick–borne encephalitis virus leads to attenuation in the mouse model. Journal of Virology. 64:5156–5159.

Iacono–Connors, et al. (1992) Cloning and sequence analysis of the genes encoding the nonstructural proteins of langat virus and comparative analysis with other flaviviruses. Virology. 188:875–880.

(List continued on next page.)

*Primary Examiner*—Ali R. Salimi
(74) *Attorney, Agent, or Firm*—Knobbe, Martens, Olson & Bear LLP

(57) ABSTRACT

A live, attenuated chimeric virus vaccine against tick-borne encephalitis virus comprising the preM and E structural genes of the tick-borne encephalitis Langat virus and the non-structural genes of the mosquito-borne dengue virus. The live chimeric vaccine was administered intraperitoneally and exhibited complete attenuation in mice while at the same time providing protection against subsequent challenge with the virulent parental Langat virus.

10 Claims, 6 Drawing Sheets

OTHER PUBLICATIONS

Iacono–Connors, et al. (1996) Characterization of Langat virus antigenic determinants defined by monoclonal antibodies to E, NS1 and preM and identification of a protective, non–neutralizing preM–specific monoclonal antibody. Virus Research. 43:125–136.

Il'Enko, et al. (1968) Experience in the study of a live vaccine made from the TP–21 strain of malayan langat virus. Bull.Wld.Hlth.Org. 39:425–431.

Irie, et la. (1989) Sequence analysis of cloned dengue virus type 2 genome (New Guinea–C strain). Gene. 75:197–311.

Klockmann, et al. (1989) Journal of Biological Standardization. 17:331–342.

Lai, et al. (1991) Infectious RNA transcribed from stably cloned full–length cDNA of dengue type 4 virus. Proc.Natl.Acad.Sci. 88:5139–5143.

Mackow, et al. (1987) The necleotide sequence of dengue type 4 virus: analysis of genes coding for nonstructural proteins. Virology. 159:217–228.

Mandl, et al. (1988) Sequence of the structural proteins of tick–borne encephalitis virus (Western Subtype) and comparative analysis with other flaviviruses. Virology. 166:197–205.

Mandl, et al. (1989) Antigenic structure of the flavivirus envelope protein E at the molecular leval, using tick–borne encephalitis virus as a model. Journal of Virology. 63:564–571.

Mandl, et al. (1991) Sequence of hte genes encoding the structural proteins of the low–virulence tick–borne flaviviruses langat TP21 and yelantsev. virology. 185:891–895.

Mandl, et al. (1991) Presence of poly(A) in a flavivirus: significant differences between the 3' noncoding regions of the genomic RNAs of tick–borne encephalitis virus strains. Journal of Virology. 65:4070–4077.

Mandl, et al. (1993) Complete genomic sequence of powassan virus: evaluation of genetic elements in tick–borne versus mosquito–borne flaviviruses. Virology. 194:173–184.

Mason, et al. (1987) Sequence of the dengue–1 virus genome in the region encoding the three structural proteins and the major nonstructural protein NS1. Virology. 161:262–267.

Mayer, et al. (1975) A live vaccine against tick–borne encephalitis: integrated studies. III. Response of man to a single dose of the E5"14"clone (langat virus). Acta.Virol. 19:229–236.

Monath, et al. (1996) Flaviviruses. Fields Virology, Third Edition Chapter 31. 961–1034.

Osatomi, et al. (1990) complete nucleotide sequences of dengue type 3 virus genome RNA. Virology. 176:643–647.

Pletnev, et al. (1990) Nucleotide sequence of the genome and complete amino acid dequence of the polyprotein of tick–borne encephalitis virus. Virology. 174:250–263.

Pletnev, et al. (1992) Construction and characterization of chimeric tick–borne encephalitis/dengue type 4 viruses. Proc.Natl.Acad.Sci. 89:10532–10536.

Pletnev, et al. (1993) Chimeric tick–borne encephalitis and dengue type 4 viruses: effects of mutations on neurovirulence in mice. Journal of Virology. 67:4956–4963.

Price, et al. (1970) Vaccination of human volunteers against Russian spring–summer (RSS) virus complex with attenuated langat E5 virus. Bull.Wld. Hlth.Org. 42:89–94.

Sanger, et al. (1977) DNA sequencing with chain–termiating inhibitors. Proc.Natl.Acad.Sci. USA 74:5463–5467.

Shamanin, et al. (1990) Differentiation of strains of tick–borne encephalitis virus by means of RNA–DNA hybridization. Journal of General Virology 71:1505–1515.

Thind, et al. (1966) A chick embryo attenuated strain (TP21 E5) of langat virus I. American Journal of Epidemilogy. 84:193–213.

Thind, et al. (1966) A chick embryo attenuated strain (TP21 E5) of langat virus II. American Journal of Epidemilogy. 84:214–224.

Wallner, et al. (1995) The flavivirus 3'–noncoding region: extensive size heterogeneity independent of evolutionaly relationships among strains of tick–borne encephalitis virus. Virology. 213:169–178.

Zhao, et al. (1986) Cloning full–length dengue type 4 viral DNA sequences: analysis of genes coding for structural proteins. Virology. 155:77–88.

Ausubel (1987) Current Protocols in Molecular Biology. Core 14 (S41) 2pgs.

Sambrook (1989) Molecular Cloning: A Laboratory Manual. Cold Spring Harbor Laboratory Press. 3pgs.

```
E5     5' - AGAUUUUCUUGCGCGUGCAUGCGUGUGCUUCAGACAGCCCAGGCAGCGACUGUGAUU----GUGGAUAUUCUUUCUGCAAGUUUUGUCGUGAACGUGUUG 96
TP21   5' - ...................................G.....................----..-.................................... 95
TBEVS  5' - ............A...........U....C.G..U...AACA........A.GUU.GAGAGAGA..C.A......GCUUG-A.CA............... 99
TBEVN  5' - ............A...........U......G......AUUA......GU..GUU.GAAAGA--..........UGUUUCUACCA............... 98
POW    5' - ............A....UG....G......U..U...UGUCC......UUCUGUUGAA-----------------------------.....GU...... 71

                                         Start
E5          AGAAAAAGACAGCUUAGGAGAACAAGAGCUGGGAAUGGCCGGGAAGGCCGUUCUAAAAGGAAAGGGGGGGGGUCCCCC 174
TP21        .............................................................................. 173
TBEVS       .................................G...............A....G..............C........ 177
TBEVN       .................................G....U.AA.......A.C.......U........C........ 176
POW         ..................................G..UUAU..U.A..AC.UCU..............C........ 149
```

*FIG. 1A*

```
                            Stop
E5     CUGGAGAGCUCAAUAUUUUAAAGCCAGAC--ACAAGGAGUCCAACCUGGAGGGCUCUUGAAAAACUC-GUCCAGAAACCAAACAAAUGAGCAAGUCAAC-  10450
TP21   ...............................--...............................-..................................-  10449
TBEVS  ...............A.C....A......UGUG.CU...CAA.........U....G.U--....AUU.......-.....A.C.A-.A..CAC-----  10435
TBEVN  ...............A.C....C......UGUG.CA...CAA....C...A.....G.-....GA.U-....G..-.....AG..A-......-....U  10451
POW    ..A........G...A.C....-.U..CAUG..UGAACAGU...AAGAACCCUAACACAGGGG------------------------------------  10400

E5     --AGGAGAUGAUAACUCGUAC----GAGCUGA-UCUCCAACACACAAGAAAA------------------------------------------------  10495
TP21   --..................----.......-....................------------------------------------------------  10494
TBEVS  ----------------------------------------------------------------------------------------------------  10435
TBEVN  CACA.....-.G.G....G..UGGA.....CUU.AAA...A.A.A..A....AAAAAAAAAAAAAAAAAAAAAAAAAAAAAAAAAAAAGCCAGAAUUGAGC  10550
POW    ----------------------------------------------------------------------------------------------------  10400

E5     ----------------------------------------------------------------------------------------------------  10495
TP21   ----------------------------------------------------------------------------------------------------  10494
TBEVS  ----------------------------------------------------------------------------------------------------  10435
TBEVN  UGAACCUGGAGAGCUCAUUAAAUACAGUCCAGACGAAACAAAACAUGACAAAGCAAAGAGGCUGAGCUAAAAGUUCCCACUACGGGACUGCUUCAUAGCG  10650
POW    ----------------------------------------------------------------------------------------------------  10400

E5     ---------------------------------AUGGUGGGAUGCGGCAACGC--GAGGCUCGUGACGGGGAAAUGAUCGCUCCCGACGCACCCCUCCA  10559
TP21   ---------------------------------...................AC...............................................  10560
TBEVS  ----------------------------------------------------------------------------------------------------  10435
TBEVN  GUUUGUGGGGGGAGGCUAGGAGGCGAAGCCACAG..CA...A...AU..GG.AGCGCGC.AGA.C.,.......G..G....A...........A-....  10749
POW    ---------------------------------......U.GCA-.CGC..A-AC..CA-.......-....GUG.G....C...........AUC.UC  10462

E5     UU-GGAGACAACUUCGUGAGAUCCCCCAGG-UGUUUA---GGGGCACACGCC-UGAGGUAAGCAA----GCCCCAGGGCGCAUUCCGGCAGCACAC-CAG  10648
TP21   ..-...........................-......---............-...........----...............-..............-...  10647
TBEVS  ----------------------------------------------------------------------....G.A.U..CC.A.....A...GU-..A  10464
TBEVN  .GAA.CA.U-...........C.....CU.ACCAGC.AAG......G..CGG-.C...GGU.AGGAAUGC......A.U.....A.........G.-...  10846
POW    ..G...A.A.UU.........C..U.AC..C..GCA.---A......CA.U.G..UA.....-..-----G...U..C.-..G.G...........U...  10553

E5     UGAGAGUGGGUGACGGGAAACUGGUCACUCCCGACGGACGUGCGCCUUGUGAAACUUUGUGAGACCCCUUGCGUCCAGAGAAGGCCGAAC-UGG--GCGUU  10745
TP21   ........................................................................................-...--.....  10744
TBEVS  .........C........CA.....GAC.......U.G.GCAUU.-...U.................CG..AC.AU..U..........A...U-..AAG  10562
TBEVN  .........C.........A.....GA........U.G.GCACU.-..AA...U.............C...A..AU..U..........A...UGCAUGA  10945
POW    .---------........G.....G.........U.AC..G.UAAAAACG..............AAAA.GCCUCCUG......UC.C.AG.AG-UUAGG  10643
```

*FIG. 1B₁*

```
E5     AUAAGGAGGCCCCAGGGGGGAAACCCCUGGGAGGAGGGAAGAGAGAAAUUGGCAACUCUCUUCAGGAUAUUUCCUCCUCCUAUACCAAA-UGUCCCCUCG  10844
TP21   .........................................................................................-..........  10843
TBEVS  .ACG.........C..AA.C.UG.UU.C...................................G....U....................-.UC...U..A  10661
TBEVN  .AGG.........C..AA.C.CG.UU.C..........................G.............U................A...-.UC.......  11044
POW    CCGUUU...AG..CCC.A.C.U.A.U.-..........G..AGA...........UCU..C..G....U......G.........U...U.UC....AG.  10742

E5     UCAGAGGGGGGGCGGUUCUUGUUCUCCCUGAGCCACCAUCACCUAGACACAGAUAGUCUGAAAAGGAGGUGAUGCGUGUCUCGGAAAAACACCCGCU-3'  10941
TP21   .................................................................................................-3'  10940
TBEVS  AU.........................................C.................C............U...A..................-3'  10758
TBEVN  GU.........................................C........G........C............U...A..................-3'  11141
POW    AA.CU.................................C..U.C..G.........C....C......A..G..U...A..................-3'  10839
```

| |
|---|
| *FIG. 1B₁* |
| *FIG. 1B₂* |

SEQUENCE LISTING

```
<160> NUMBER OF SEQ ID NOS: 29

<210> SEQ ID NO 1
<211> LENGTH: 174
<212> TYPE: DNA
<213> ORGANISM: Flavivirus, Langat

<400> SEQUENCE: 1

agauuuucuu gcgcgugcau gcgugugcuu cagacagccc aggcagcgac ugugauugug     60

gauauucuuu cugcaaguuu ugucgugaac guguugagaa aaagacagcu uaggagaaca    120

agagcuggga auggccggga aggccguucu aaaaggaaag gggggggguc cccc          174

<210> SEQ ID NO 2
<211> LENGTH: 173
<212> TYPE: DNA
<213> ORGANISM: Flavivirus, Langat

<400> SEQUENCE: 2

agauuuucuu gcgcgugcau gcgugugcuu cagagagccc aggcagcgac ugugauugug     60

auauucuuuc ugcaaguuuu gucgugaacg uguugagaaa aagacagcuu aggagaacaa    120

gagcugggaa uggccgggaa ggccguucua aaaggaaagg gggggggucc ccc           173

<210> SEQ ID NO 3
<211> LENGTH: 177
<212> TYPE: DNA
<213> ORGANISM: Flavivirus, Tick-borne Encephalitis

<400> SEQUENCE: 3

agauuuucuu gcacgugcau gcguuugcuc cggauagcaa cagcagcgac agguuugaga     60

gagagacaau cuuucgcuug aucagucgug aacguguuga gaaaaagaca gcuuaggaga    120

acaagagcug ggauggccg ggaaggccau ucugaaagga aagggggcg guccccc          177
```

-continued

<210> SEQ ID NO 4
<211> LENGTH: 176
<212> TYPE: DNA
<213> ORGANISM: Flavivirus, Tick-borne Encephalitis

<400> SEQUENCE: 4
agauuuucuu gcacgugcau gcguuugcuu cggacagcau uagcagcggu ugguuugaaa 60
gagauauucu uuuguuucua ccagucguga acguguugag aaaaagacag cuuaggagaa 120
caagagcugg ggauggucaa gaaggccauc cuaaaaggua agggggcgg uccccc 176

<210> SEQ ID NO 5
<211> LENGTH: 149
<212> TYPE: DNA
<213> ORGANISM: Flavivirus, Tick-borne Encephalitis

<400> SEQUENCE: 5
agauuuucuu gcacgugugu gcgggugcuu uagucagugu ccgcagcguu cuguugaacg 60
ugaguguguu gagaaaaaga cagcuuagga gaacaagagc ugggaguggu uaugaugacc 120
acuucuaaag gaaaggggg cgguccccc 149

<210> SEQ ID NO 6
<211> LENGTH: 587
<212> TYPE: DNA
<213> ORGANISM: Flavivirus, Langat

<400> SEQUENCE: 6
cuggagagcu caauauuuua aagccagaca caaggagucc aaccuggagg gcucuugaaa 60
aacucgucca gaaaccaaac aaaugagcaa gucaacagga gaugauaacu cguacgagcu 120
gaucuccaac acacaagaaa aauggugga ugcggcaacg cgaggcucgu gacggggaaa 180
ugaucgcucc cgacgcaccc cuccauugga gacaacuucg ugagaucccc cagguguuua 240
ggggcacacg ccugagguaa gcaagcccca gggcgcauuc cggcagcaca ccagugagag 300
uggugacggg aaacugguca cucccgacgg acgugcgccu ugugaaacuu ugugagaccc 360
cuugcgucca gagaaggccg aacugggcgu uauaaggagg ccccaggggg gaaaccccug 420
ggaggaggga agagagaaau uggcaacucu cuucaggaua uuuccuccuc cuauaccaaa 480
uguccccucg ucagaggggg ggcgguucuu guucucccug agccaccauc accuagacac 540
agauagucug aaaaggaggu gaugcguguc ucggaaaaac acccgcu 587

<210> SEQ ID NO 7
<211> LENGTH: 587
<212> TYPE: DNA
<213> ORGANISM: Flavivirus, Langat

<400> SEQUENCE: 7
cuggagagcu caauauuuua aagccagaca caaggagucc aaccuggagg gcucuugaaa 60
aacucgucca gaaaccaaac aaaugagcaa gucaacagga gaugauaacu cguacgagcu 120
gaucuccaac acacaagaaa aauggugga ugcggcaacg cacgaggcuc gugacgggga 180
aaugaucgcu cccgacgcac cccuccauug gagacaacuu cgugagaucc cccagguguu 240
uaggggacac gccugaggua agcaagcccc agggcgcauc cggcagcaca ccagugagag 300
uggugacggg aaacugguca cucccgacgg acgugcgccu ugugaaacuu ugugagaccc 360
cuugcgucca gagaaggccg aacugggcgu uauaaggagg ccccaggggg gaaaccccug 420
ggaggaggga agagagaaau uggcaacucu cuucaggaua uuuccuccuc cuauaccaaa 480

-continued uguccccucg ucagaggggg ggcgguucuu guucucccug agccaccauc accuagacac 540
agauagucug aaaaggaggu gaugcguguc ucggaaaaac acccgcu 587

<210> SEQ ID NO 8
<211> LENGTH: 414
<212> TYPE: DNA
<213> ORGANISM: Flavivirus, Tick-borne Encephalitis

<400> SEQUENCE: 8
cuggagagcu caauaaucua aaaccagacu gugacugagc aaaaccugga gugcucguua 60
aacauugucc agaaccaaaa acaaaacaca cccccggagu gcccuacggc aacacgucaa 120
ugagaguggc gacgggaaca uggucgaccc cgacguaggg cauucuguua aacuuuguga 180
gacccccggc accaugauaa ggccgaacau ggugcaagaa cgggaggccc ccggaagcau 240
gcuuccggga ggagggaaga gagaaauugg caacucucuu cgggauuuuu ccuccuccua 300
uaccaaauuc cccuucaaua gaggggggc gguucuuguu cucccugagc caccaucacc 360
cagacacaga uagucugaca aggaggugau gugugacucg gaaaaacacc cgcu 414

<210> SEQ ID NO 9
<211> LENGTH: 785
<212> TYPE: DNA
<213> ORGANISM: Flavivirus, Tick-borne Encephalitis

<400> SEQUENCE: 9
cuggagagcu caauaaucua aacccagacu gugacagagc aaaacccgga aggcucguaa 60
aagauugucc ggaaccaaaa gaaaagcaag caacucacag agauagagcu cggacuggag 120
agcucuuuaa acaaaaaaaa aaaaaaaaaa aaaaaaaaaa aaaaaaaaaa aaaaaaaaaa 180
agccagaauu gagcugaacc uggagagcuc auuaaauaca guccagacga aacaaaacau 240
gacaaagcaa agaggcugag cuaaaaguuc ccacuacggg acugcuucau agcgguuugu 300 gggggaggc uaggaggcga agccacagau cauggaauga ugcggcagcg cgcgagagcg 360
acggggaagu ggucgcaccc gacgcaccau ccaugaagca auacuucgug agaccccccc 420
ugaccagcaa agggggcaga ccggucaggg gugaggaaug cccccagagu gcauuacggc 480
agcacgccag ugagaguggc gacgggaaaa uggucgaucc cgacguaggg cacucugaaa 540
aauuuuguga gacccccugc aucaugauaa ggccgaacau ggugcaugaa aggggaggcc 600
cccggaagca cgcuuccggg aggagggaag agagaaauug gcagcucucu ucaggauuuu 660
uccuccuccu auacaaaauu cccccucggu agaggggggg cgguucuugu ucucccugag 720
ccaccaucac ccagacacag guagucugac aaggagguga ugugugacuc ggaaaaacac 780
ccgcu 785

<210> SEQ ID NO 10
<211> LENGTH: 501
<212> TYPE: DNA
<213> ORGANISM: Flavivirus, Tick-borne Encephalitis

<400> SEQUENCE: 10
cuagagagcu cgauaaucua aacuagcaug acugaacagu caaaagaacc cuaacacagg 60
ggauggugug gcagcgcaca acgacaucgu gacgggagug ggucgccccc gacgcaccau 120
ccucuuggga aaaauuuucg ugagacccuc acggcuggca aagggcacca gucguguagu 180
aagaaggccc uggcccagug cggcagcaca cucagugacg ggaaaguggu cgcucccgac 240

-continued

```
guaacugggu aaaaacgaac uuugugagac caaaaggccu ccuggaaggc ucaccaggag    300

uuaggccguu uaggagcccc cgagcauaac ucgggaggag ggaggaagaa aauuggcaau    360

cuuccucggg auuuuuccgc cuccuauacu aaauuucccc caggaaacug ggggggcggu    420

ucuuguucuc ccugagccac caccauccag gcacagauag ccugacaagg agauggugug    480

ugacucggaa aaacacccgc u                                              501


<210> SEQ ID NO 11
<211> LENGTH: 27
<212> TYPE: DNA
<213> ORGANISM: Artificial Sequence
<220> FEATURE:
<223> OTHER INFORMATION: Synthetic Oligonucleotide complementary to DEN4

<400> SEQUENCE: 11

gaccgacaag gacagttcca aatcgga                                         27


<210> SEQ ID NO 12
<211> LENGTH: 21
<212> TYPE: DNA
<213> ORGANISM: Artificial Sequence
<220> FEATURE:
<223> OTHER INFORMATION: Synthetic PCR primer

<400> SEQUENCE: 12

gctccggggt gtaagtccat t                                               21


<210> SEQ ID NO 13
<211> LENGTH: 40
<212> TYPE: DNA
<213> ORGANISM: Artificial Sequence
<220> FEATURE:
<223> OTHER INFORMATION: Synthetic PCR primer

<400> SEQUENCE: 13

tctctatctg ccaagtctgg atccttgagc tctctatcca                           40


<210> SEQ ID NO 14
<211> LENGTH: 11
<212> TYPE: PRT
<213> ORGANISM: Artificial Sequence
<220> FEATURE:
<223> OTHER INFORMATION: Synthetic chimeric flavivirus protein sequence

<400> SEQUENCE: 14

Met Ala Gly Lys Gly Leu Asn Ser Arg Asn Thr
 1               5                  10


<210> SEQ ID NO 15
<211> LENGTH: 54
<212> TYPE: DNA
<213> ORGANISM: Artificial Sequence
<220> FEATURE:
<223> OTHER INFORMATION: Synthetic chimeric flavivirus nucleic acid
      sequence

<400> SEQUENCE: 15

agagagcaga tctctggaaa aatggccggg aagggcttga actcgaggaa cact           54


<210> SEQ ID NO 16
<211> LENGTH: 17
<212> TYPE: PRT
<213> ORGANISM: Synthetic chimeric flavivirus protein sequence

<400> SEQUENCE: 16
```

-continued

Ile Leu Gln Arg Arg Gly Ser Arg Arg Thr Gly Leu Asn Ser Arg Asn
1 5 10 15

Thr

<210> SEQ ID NO 17
<211> LENGTH: 51
<212> TYPE: DNA
<213> ORGANISM: Artificial Sequence
<220> FEATURE:
<223> OTHER INFORMATION: Synthetic chimeric flavivirus nucleic acid sequence

<400> SEQUENCE: 17
atcctgcagc gccgaggaag tagaaggacg ggcttgaact cgaggaacac t 51

<210> SEQ ID NO 18
<211> LENGTH: 17
<212> TYPE: PRT
<213> ORGANISM: Artificial Sequence
<220> FEATURE:
<223> OTHER INFORMATION: Synthetic chimeric flavivirus protein sequence

<400> SEQUENCE: 18

Leu Asn Gly Arg Lys Arg Ser Ile Ile Asp Gly Leu Asn Ser Arg Asn
1 5 10 15

Thr

<210> SEQ ID NO 19
<211> LENGTH: 51
<212> TYPE: DNA
<213> ORGANISM: Artificial Sequence
<220> FEATURE:
<223> OTHER INFORMATION: Synthetic chimeric flavivirus nucleic acid sequence

<400> SEQUENCE: 19
ctgaacggga gaaaaagatc gatcattgac ggcttgaact cgaggaacac t 51

<210> SEQ ID NO 20
<211> LENGTH: 17
<212> TYPE: PRT
<213> ORGANISM: Artificial Sequence
<220> FEATURE:
<223> OTHER INFORMATION: Synthetic chimeric flavivirus protein sequence

<400> SEQUENCE: 20

Leu Asn Gly Arg Lys Arg Ser Ala Val Asp Gly Leu Asn Ser Arg Asn
1 5 10 15

Thr

<210> SEQ ID NO 21
<211> LENGTH: 51
<212> TYPE: DNA
<213> ORGANISM: Artificial Sequence
<220> FEATURE:
<223> OTHER INFORMATION: Synthetic chimeric flavivirus nucleic acid sequence

<400> SEQUENCE: 21
ctgaacggga gaaaaaggtc tgcagttgac ggcttgaact cgaggaacac t 51

<210> SEQ ID NO 22
<211> LENGTH: 17
<212> TYPE: PRT

-continued

<213> ORGANISM: Artificial Sequence
<220> FEATURE:
<223> OTHER INFORMATION: Synthetic chimeric flavivirus protein sequence

<400> SEQUENCE: 22

Met Ala Phe Ser Leu Val Ala Arg Glu Arg Gly Leu Asn Ser Arg Asn
1 5 10 15

Thr

<210> SEQ ID NO 23
<211> LENGTH: 51
<212> TYPE: DNA
<213> ORGANISM: Artificial Sequence
<220> FEATURE:
<223> OTHER INFORMATION: Synthetic chimeric flavivirus nucleic acid sequence

<400> SEQUENCE: 23
atggcgtttt ccttggttgc aagagagaga ggcttgaact cgaggaacac t 51

<210> SEQ ID NO 24
<211> LENGTH: 17
<212> TYPE: PRT
<213> ORGANISM: Artificial Sequence
<220> FEATURE:
<223> OTHER INFORMATION: Synthetic chimeric flavivirus protein sequence

<400> SEQUENCE: 24

Gly Thr Asn Ser Arg Asn Pro Thr Arg Gly Arg Arg Ser Trp Pro Leu
1 5 10 15

Asn

<210> SEQ ID NO 25
<211> LENGTH: 51
<212> TYPE: DNA
<213> ORGANISM: Artificial Sequence
<220> FEATURE:
<223> OTHER INFORMATION: Synthetic chimeric flavivirus nucleic acid sequence

<400> SEQUENCE: 25
ggcacgaact cgaggaaccc aaccaggggg agacgatcgt ggcctcttaa c 51

<210> SEQ ID NO 26
<211> LENGTH: 17
<212> TYPE: PRT
<213> ORGANISM: Artificial Sequence
<220> FEATURE:
<223> OTHER INFORMATION: Synthetic chimeric flavivirus protein sequence

<400> SEQUENCE: 26

Gly Thr Asn Ser Arg Asn Pro Thr Gly Thr Gly Trp Ile Arg Lys Lys
1 5 10 15

Arg

<210> SEQ ID NO 27
<211> LENGTH: 51
<212> TYPE: DNA
<213> ORGANISM: Artificial Sequence
<220> FEATURE:
<223> OTHER INFORMATION: Synthetic chimeric flavivirus nucleic acid sequence

<400> SEQUENCE: 27
ggcacgaact cgaggaaccc aaccggcacg ggctggattc gaaagaaaag a 51

-continued

```
<210> SEQ ID NO 28
<211> LENGTH: 17
<212> TYPE: PRT
<213> ORGANISM: Artificial Sequence
<220> FEATURE:
<223> OTHER INFORMATION: Synthetic chimeric flavivirus protein sequence

<400> SEQUENCE: 28

Gly Ala Ser Arg Arg Ser Phe Asn Glu Ser Gly Arg Arg Ser Ile Thr
 1               5                  10                  15

Leu


<210> SEQ ID NO 29
<211> LENGTH: 51
<212> TYPE: DNA
<213> ORGANISM: Artificial Sequence
<220> FEATURE:
<223> OTHER INFORMATION: Synthetic chimeric flavivirus nucleic acid
      sequence

<400> SEQUENCE: 29

ggagcctcaa gacgatcgtt taatgagtct ggaagaagat ctataactct c             51
```

CHIMERIC VACCINE AGAINST TICK-BORNE ENCEPHALITIS VIRUS

RELATED APPLICATIONS

This application is a continuation and claims the benefit of priority of U.S. patent application Ser. No. 09/518,036 filed Mar. 3, 2000, now U.S. Pat. No. 6,497,884, which is a continuation and claims the benefit of priority of International Pat. Appl. No. PCT/US98/21308 having international filing date of Oct. 8, 1998, designating the United States of America and published in English, which claims the benefit of priority of U.S. Prov. Appl. No. 60/061,441, filed Oct. 8, 1997, all of which are hereby incorporated by reference in their entireties.

FIELD OF THE INVENTION

The present invention relates to a chimeric virus vaccine against tick-borne encephalitis virus (TBEV) and its other virulent relatives. More specifically, the invention relates to a chimeric virus comprising the Langat (LGT) virus preM and E structural protein genes linked to the non-structural protein genes of a mosquito-borne flavivirus.

BACKGROUND OF THE INVENTION

The Flaviviridae family encompasses more than sixty antigenically related, positive strand RNA viruses within the arthropod-borne flavivirus genus, many of which are important human pathogens (Monath et al., Flaviviruses, in Virology, B. N. Fields et al., Eds., Raven Press, New York, pp. 961–1035, 1996). These include the mosquito-borne yellow fever virus, Japanese encephalitis virus, dengue viruses (DEN) and the tick-borne encephalitis viruses (TBEV), the latter being endemic in most European countries, Russia, India and North China. TBEV is transmitted exclusively by ticks and can be divided into two serologically distinguishable subtypes: the Eastern subtype (prototype strain Sofjin), prevalent in Siberian and Far Eastern regions of Russia, and the Western subtype (prototype strain Neudorfl), common in eastern and central Europe. TBEV causes a serious encephalitic illness with a mortality rate ranging from 1 to 30%.

Flaviviruses share the same genome organization: 5'-C-preM-E-NS1-NS2A-NS2B-NS3-NS4A-NS4B-NS5-3' in which the first three genes code the capsid (C), premembrane (preM) and envelope (E) proteins, while the remainder of the genes encode nonstructural proteins. Homology between mosquito-borne and tick-borne flaviviruses is relatively low (Chambers et al., Annu. Rev. Microbiol. 44:649–688, 1990; Pletnev et al., Virology 174:250–263, 1990). However, homology among mosquito-borne flaviviruses or among tick-borne flaviviruses is relatively high (Iacoco-Connors et al., Virology 188:875–880, 1992).

Four serotypes of dengue virus are known (type 1 to type 4) which are distinguishable by plaque reduction neutralization using serotype-specific monoclonal antibodies and by less specific tests using polyclonal sera (Bancroft et al., Pan Am. Hlth. Org. Sci. Publ. 375:175–178, 1979; Henchal et al., Am. J. Trop. Med. Hyg. 31:548–555, 1982). The four dengue serotypes share a common genome organization. The complete nucleotide sequences have been determined for dengue virus types 3 and 4 and several strains of type 2 virus including the mouse-neurovirulent New Guinea C mutant (Mackow et al., Virology 159:217–228, 1987; Zhao et al., Virology 155:77–88, 1986; Osatomi et al., Virology 176:643–647, 1990; Irie et al., Gene 75:197–211, 1989; Mason et al., Virology 161:262–267, 1987; Hahn et al., Virology 162:167–180, 1988).

Despite the considerable evolutionary distance between DEN and TBEV, a viable chimeric flavivirus was constructed which contained the C-preM-E or preM-E structural protein genes of a virulent Far Eastern Russian TBEV with the remaining nonstructural protein genes and 5'- and 3'-noncoding sequences derived from DEN4 [TBEV(CME)/DEN4 and TBEV(ME)/DEN4, respectively] (Pletnev et al., Proc. Natl. Acad. Sci. U.S.A. 89:10532–10536, 1992).

TBEV(ME)/DEN4 retained the neurovirulence in mice of its TBEV parent from which its preM and E genes were derived, but it lacked the peripheral neurovirulence of TBEV, i.e. the ability to spread from a peripheral site to the central nervous system (CNS) and cause fatal encephalitis. However, mice previously inoculated with the chimeric virus by a peripheral route were completely resistant to subsequent intraperitoneal challenge with a lethal dose of the highly virulent TBEV. Neurovirulence of this chimera was significantly reduced by a single mutation introduced into its preM, E or nonstructural protein 1 (NS1) viral protein (Pletnev et al., J. Virol. 67:4956–4963, 1993). These amino acid substitutions also caused a restriction in viral replication in tissue cultures of both simian and mosquito cells. Nonetheless, parenteral inoculation of these further attenuated chimeric mutants induced complete resistance in mice to fatal encephalitis caused by intracerebral inoculation of the neurovirulent TBEV(ME)/DEN4 chimera.

Langat (LGT) virus is the least virulent of all TBEV-complex flaviviruses, but is closely related antigenically to the highly virulent Far Eastern TBEV (Calisher et al., J. Gen. Virol. 70:37–43, 1989; DeMadrid et al., J. Gen. Virol. 23:91–96, 1974; Iacoco-Connors et al., Virus Res. 43:125–136, 1996) and has a high level of sequence homology thereto (Iacoco-Connors et al., Virology 188:875–880, 1992; Mandl et al., Virology 185:891–895, 1991; Shamanin et al., J. Gen. Virol. 71:1505–1515, 1990). LGT virus was tested as an experimental live vaccine against TBEV during the early 1970s (Ilenko et al., Bull. Wld. Hlth. Org. 39:425–431, 1968; Mayer et al., Acta. Virol. 19:229–236, 1975; Price et al., Bull. Wld. Hlth. Org. 42:89–94, 1970). Several LGT strains which were attenuated for mice and monkeys were isolated and tested in 800,000 adults; however, clinical trials were discontinued when vaccination with one of the most attenuated vaccine candidates, Yelantsev virus, was associated with a very low frequency of encephalitis, i.e. one case per 20,000 vaccinations (Mandl et al., supra.)

Currently, an experimental TBEV vaccine produced by formalin inactivation of TBEV is available; however, this vaccine has several limitations. For example, the vaccine is not strongly immunogenic, therefore repeated vaccinations are required to generate a protective immune response. Even when antibody responses to the vaccine are present, the vaccine fails to provide protective responses to the virus in 20% of the population. Therefore, there remains the need for a safe, more effective vaccine against TBEV. The present invention provides such a vaccine.

SUMMARY OF THE INVENTION

One embodiment of the present invention is a viable chimeric recombinant flavivirus, comprising a first region of nucleic acid operably encoding preM and E structural proteins of Langat virus operably linked to a second region of nucleic acid operably encoding non-structural proteins of a mosquito-borne flavivirus. Preferably, the Langat virus is the Langat wild type virus strain TP21 or its further attenuated mutant, Langat strain E5. Advantageously, the mosquito-borne flavivirus is a dengue virus. In one aspect of this preferred embodiment, the dengue virus is type 4. Alternatively, the mosquito-borne flavivirus is yellow fever virus. According to another aspect of this preferred embodiment, the first region of nucleic acid also operably encodes capsid protein from the mosquito-borne flavivirus or from Langat virus. In yet another aspect of this preferred embodiment, the recombinant flavivirus further comprising at least one mutation. Preferably, the recombinant flavivirus is incorporated within an expression vector. Advantageously, the expression vector is a plasmid.

The present invention also provides a host cell stably transformed with the recombinant flavivirus described above in a manner allowing expression of said DNA construct. Preferably, the host cell is prokaryotic. In another aspect of this preferred embodiment, the tick-borne encephalitis virus is selected from the group consisting of the Eastern, Western, Omsk hemorrhagic fever, louping ill, Kyasanur forest disease, Negishi, or Powassan viruses.

Another embodiment of the present invention is a vaccine against tick-borne encephalitis virus, comprising the chimeric recombinant flavivirus described above in a pharmaceutically acceptable carrier. Another embodiment is the vaccination of milk producing mammals against tick-borne encephalitis virus infection. Still another embodiment of the present invention encompasses an immunogenic composition comprising the chimeric recombinant flavivirus described above in a pharmaceutically acceptable carrier.

The present invention also provides a method of preventing TBEV infection in a mammal, comprising the step of administering to the mammal an effective TBEV-preventing amount of a chimeric recombinant flavivirus, the chimeric flavivirus comprising a first region of nucleic acid operably encoding C, preM and E structural proteins of Langat virus, or C protein of the mosquito-borne flavivirus plus preM and E structural proteins of Langat virus, operably linked to a second region of nucleic acid operably encoding non-structural proteins of a mosquito-borne flavivirus, in a pharmaceutically acceptable carrier. Preferably, the mammal is a human. Advantageously, the administering step is intranasal, intradermal, subcutaneous, intramuscular, or intravenous. In one aspect of this preferred embodiment, the effective TBEV-preventing amount is between about 1 $\mu$g and 1,000 $\mu$g. The method may further comprise administering one or more booster injections of the chimeric flavivirus.

The present invention also contemplates a method of stimulating an immune response directed against the chimeric recombinant flaviviruses discussed above, in a mammal, comprising the step of administering to the mammal an effective TBEV-preventing amount of a chimeric recombinant flavivirus, the chimeric flavivirus comprising a first region of nucleic acid operably encoding C, preM and E structural proteins of Langat virus, or C protein of the mosquito-borne flavivirus plus preM and E structural proteins of Langat virus, operably linked to a second region of nucleic acid operably encoding non-structural proteins of a mosquito-borne flavivirus, in a pharmaceutically acceptable carrier.

BRIEF DESCRIPTION OF THE DRAWINGS

FIG. 1A shows a sequence alignment of the 5' terminal noncoding region (NCR) sequences of the attenuated tick-borne flavivirus LGT strain TP21 (SEQ ID NO: 1), its more attenuated derivative LGT E5 strain (SEQ ID NO: 2) and the virulent TBEV strains Sofjin (TBEVS; SEQ ID NO: 3) and Neudoerfl (TBEVN; SEQ ID NO: 4) and the virulent North American Strain Powassan (POW; SEQ ID NO: 5). Nucleotides identical to the sequence of LGT strain E5 are depicted by dots, and gaps introduced for the alignment are shown by dashes. Sequence numbers are shown to the right. Initiation and stop codons are underlined.

FIG. 1B shows a sequence alignment of the 3' terminal-NCR sequences of the attenuated tick-borne flavivirus LGT strain TP21 (SEQ ID NO: 6), its more attenuated derivative LGT E5 strain (SEQ ID NO: 7) and the virulent TBEV strains Sofjin (TBEVS; SEQ ID NO: 8) and Neudoerfl (TBEVN; SEQ ID NO: 9) and the virulent North American strain Powassan (POW; SEQ ID NO: 10). Nucleotides identical to the sequence of LGT strain E5 are depicted by dots, and gaps introduced for the alignment are shown by dashes. Sequence numbers are shown to the right. Initiation and stop codons are underlined.

DETAILED DESCRIPTION OF THE INVENTION

Figure 2A:
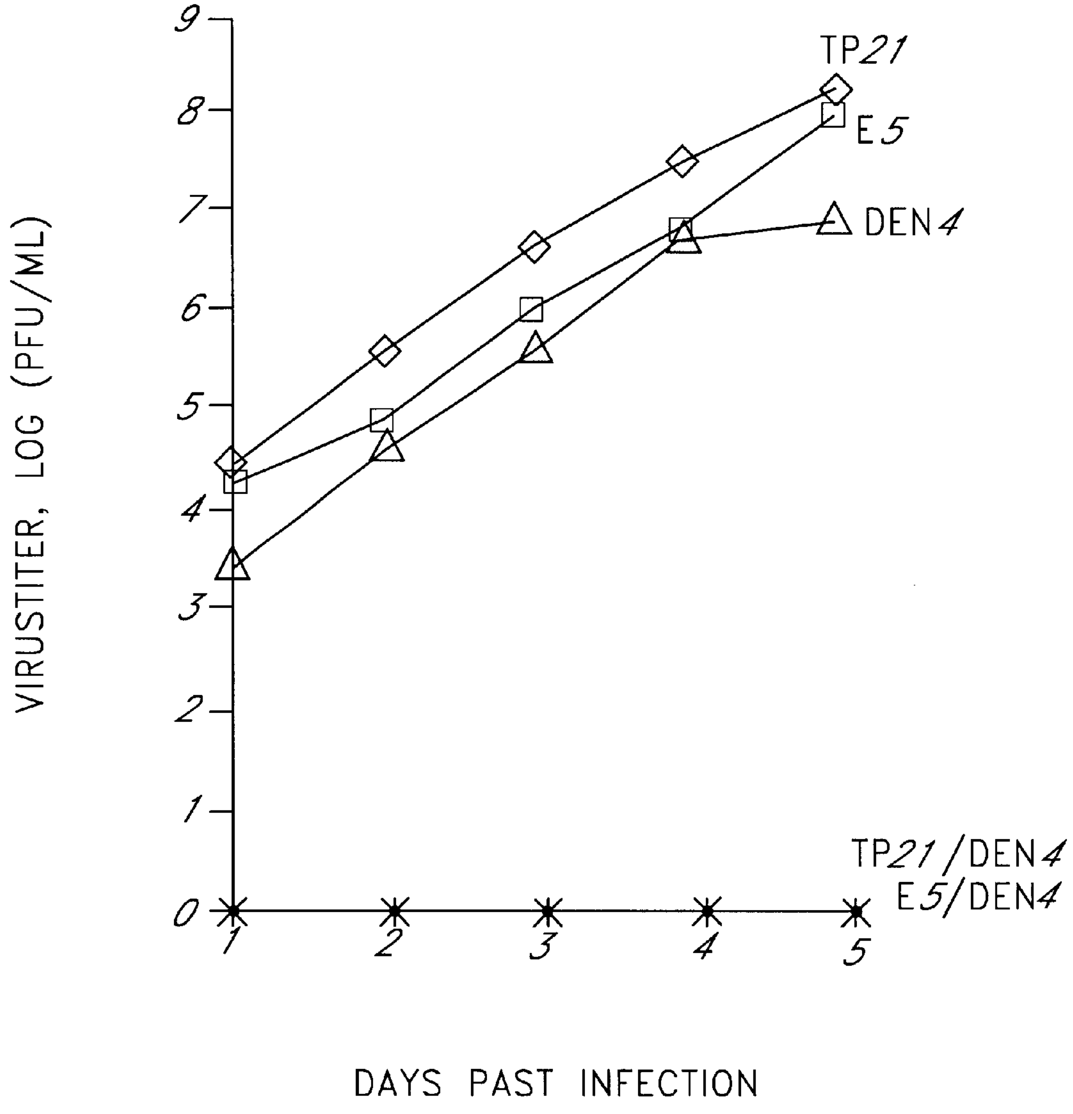
FIGS. 2A–2C illustrate the growth of parental and chimeric flaviviruses in simian $LLCMK_2$ (FIG. 2A), simian Vero (FIG. 2B) and mosquito cells (FIG. 2C). Chimeric virus inocula were grown in mosquito cells. Parental LGT TP21 and E5 virus inocula were grown in simian Vero cells. DEN4 parental virus inoculum for mosquito cells and simian cells were grown in mosquito cells and simian Vero cells, respectively. Simian $LLCMK_2$ or Vero cells were infected with: (i) DEN4, TP21 or E5 virus at a multiplicity of infection (MOI) of 0.01, or (ii) chimeric TP21/DEN4 or E5/DEN4 virus at a MOI of 0.5. Mosquito C6/36 cells were infected with: (i) DEN4, TP21/DEN4 or E5/DEN4 virus at a MOI of 0.01 or (ii) with TP21 or E5 virus at a MOI of 1,000. Cells were harvested at the indicated day after infection and virus titer was determined by a plaque assay on the same cells used for study of virus replication. Plaques were counted 7 or 8 days post-infection. Reduction in plaque size indicates that the viruses exhibit a growth-restriction phenotype.

The present invention includes the observation that LGT/DEN4 chimeric viruses containing the preM and E structural proteins of LGT strains TP21 or E5 exhibited restriction of growth and plaque formation when inoculated into simian cell cultures. E5 is a more attenuated derivative of TP21 (Thind et al., Amer. J. Epidemiol. 84:198–213, 1966) which differs therefrom by 24 nucleotides which produces 11 coding changes, four of which are in the E protein (Table 2). These LGT/DEN4 chimeras were at least 5,000 times less neurovirulent than parental LGT viruses in suckling mice (Table 3). Also, these chimeras lacked detectable evidence of neuroinvasiveness following intraperitoneal inoculation of $10^5$ plaque forming units (PFU) in Swiss mice or $10^7$ PFU in SCID mice. In contrast, TP21 or E5 had intraperitoneal $LD_{50}$ values in SCID mice of 0.004 and 0.06 PFU, respectively. Although the chimeras lacked detectable neuroinvasiveness, even in SCID mice, intraperitoneal inoculation of 10 or $10^3$ PFU of either virus induced LGT neutralizing antibodies and resistance to fatal encephalitis caused by LGT TP 21 challenge. Thus, the LGT/DEN4 construct is useful as a vaccine for any strain of TBEV, including the Eastern and Western subtypes, all of which are closely related antigenically. Although DEN4 was used as a mosquito-borne flavivirus to produce the chimeric vaccine, the use of other strains of Dengue virus (i.e. types 1, 2 and 3) is also contemplated due to the high level of sequence homology and close antigenic relationship of these other types with type 4. Further, the use of a chimeric vaccine comprising any mosquito-borne flavivirus nonstructural protein cDNA (including yellow fever virus), optionally including the C protein from a mosquito-borne flavivirus or from Langat virus, in combination with LGT cDNA encoding the preM and E proteins is also within the scope of the present invention. These chimeric constructs include point mutations, insertions, deletions and substitutions in any of the viral genes which does not compromise the ability of the construct to provide protective immunity against challenge with the virulent TBEV parental virus.

The complete nucleotide sequence was determined for the genome of wild type LGT virus (TP21 strain) and its more attenuated E5 derivative produced by multiple passages in chick embryo tissue. Full-length DEN4 cDNA was used to engineer chimeric LGT/DEN4 expression vector constructs by substituting the structural or nonstructural protein genes of LGT TP21 or LGT E5 for the corresponding DEN4 genes using methods well known in the art of molecular biology which are described in such reference as Sambrook et al. (Molecular Cloning: a Laboratory Manual, Cold Spring Harbor Press, Cold Spring Harbor N.Y., 1988; Ausubel, Current Protocols in Molecular Biology, 1989). Only two of the 16 chimeric constructs tested (depicted in Table 1A) were viable, as judged by their ability to grow and produce viral particles in culture (Table 1B). These two chimeric viruses contained the preM and E genes of LGT virus strain TP21 or strain E5 and all other sequences from DEN4. These chimeras differed in their LGT-derived sequences at only four amino acid positions in the E protein (Table 2). The chimeric TP21/DEN4 and E5/DEN4 viruses were analyzed for their efficiency of growth in cell culture, mouse neurovirulence and neuroinvasiveness (peripheral neuroinvasiveness), immunogenicity and protective efficacy. These properties were compared to those of their LGT parents as well as those described previously for the highly virulent, closely related TBEV.

Chimerization of LGT TP21 or LGT E5 with mosquito-borne DEN4 significantly reduced replicative capacity of the resulting virus in simian cells compared to either parental virus. Significant reduction in neurovirulence was also observed when TP21 or E5 was chimerized with DEN4, suggesting that this might be a general phenomenon for viruses of the tick-borne flavivirus group. Thus, the chimeric viruses appeared to retain the very low neurovirulence of their mosquito-borne DEN4 parent rather than the higher mouse neurovirulence of their tick-borne LGT virus parent.

The present invention also relates to a recombinant chimeric DNA construct comprising a DNA fragment encoding LGT virus preM and E proteins and dengue virus nonstructural proteins, and a vector. This DNA fragment may encode the wild type proteins, or mutant proteins thereof including point mutations, insertions, deletions and the like which do not compromise the safety and efficacy of the vaccine produced from the chimeric construct. The safety and efficacy of any such chimeric virus can be determined using the methods described herein without undue experimentation.

In another embodiment, the invention relates to a chimeric vaccine for humans against TBEV, comprising DNA encoding LGT wild type TP21 or E5 preM and E proteins and dengue virus nonstructural proteins. These chimeric vaccines are evaluated in non-human primates for: (1) replicative efficiency as measured by extent and duration of viremia; (2) virulence as measured by neurologic signs following direct intranasal or intracerebral inoculation or peripheral inoculation; (3) immunogenicity as indicated by the type and magnitude of antibody response following viral infection, satisfactory immunogenicity and protective efficacy; and (4) protective efficacy as measured by resistance to challenge with virulent tick-borne encephalitis virus following immunization. Chimeric vaccines that show markedly reduced virulence but retain sufficient immunogenicity in monkeys are evaluated during clinical trials in humans.

For use as a vaccine, the chimeric flaviviruses of the invention are formulated with a pharmaceutically acceptable carrier and parenterally administered to a mammal, preferably a human. Pharmaceutically acceptable means that the agent should be acceptable in the sense of being compatible with the other ingredients of the formulation as well as non-injurious to the patient. Such carriers include phosphate buffered saline (PBS) and lactate Ringer's solution. Contemplated modes of administration of the vaccine include intradermal, intravenous, subcutaneous and any other route which allows entry of the vaccine into the body at a peripheral site, i.e. skin, muscle, subcutaneous tissue, etc. The amount of the vaccine preparation administered to a mammal is typically between about 1 $\mu$g and 1,000 $\mu$g, preferably between about 50 $\mu$g and 500 $\mu$g. The method may further comprise administering one or more booster injections of the chimeric flavivirus in an amount between about 1 $\mu$g and about 1,000 $\mu$g. Although the precise amount of recombinant virus will vary depending on the individual, this amount can be optimized using routine dose-response experiments well known to those of ordinary skill in the art.

LGT and DEN4 flaviviruses were obtained, chimerized and evaluated for neurovirulence and protective efficacy against parent LGT virus challenge as described in the examples provided below.

EXAMPLE 1

Virus Sources and Isolation of Viruses

LGT wild type strain TP21 was originally isolated from ticks in Malaya in 1956 (Gordon-Smith, Nature 178:581–582, 1956). It was then passaged 11 times in mouse brain and twice in simian Vero cells. The LGT TP21 strain used herein was obtained from Dr. R. Shope (Yale University, New Haven, Conn.) from the Rockefeller Foundation Collection. The LGT attenuated strain E5 was derived from the TP21 strain by 42 passages in 7-day-old chick embryos and had an additional passage in simian Vero cells (Thind et al., Amer. J. Epidemiol. 84:198–213, 1966; Thind et al., Amer. J. Epidemiol. 84:214–224, 1966). This virus was obtained from Dr. J. Huggins (USAMRIID, Frederick, Md.). Langat viruses were plaque purified three times on Vero cells under soft agar prior to preparation of virus stocks that titered $2\times10^9$ plaque forming units (pfu)/ml for TP21 virus and $1.2\times10^9$ pfu/ml for E5 virus. Vero cells were grown at 37° C. in Eagle's minimum essential medium (MEM) plus 10% fetal calf serum (FCS) and incubated in an atmosphere of 5% $CO_2$. DEN4(clone 2A) virus rescued from the full-length cDNA construct of dengue type 4 strain 814669 genome was used as the parental DEN4 virus (Lai et al., Proc. Natl. Acad. Sci. U.S.A. 88:5139–5143, 1991). All of these viruses are generally available from the scientific research community.

EXAMPLE 2

Genome Sequences of Langat Viruses

Purification of LGT and isolation of its RNA were performed as described previously for TBEV (Pletnev et al., Virology 174:250–263, 1990). First strand cDNA was synthesized using the reverse transcriptase SuperScript™ purification system (GibcoBRL, Life Technologies) and a synthetic oligonucleotide primer complementary to the conserved 22 3'-terminal nucleotides of TBEV strains (Mandl et al., J. Virol. 65:4070–4077, 1991; Wallner et al., Virology 213:169–178, 1995) or the same 3'-terminal sequence of Powassan virus genome (Mandl et al., Virology 194:173–184, 1993). The polymerase chain reaction (PCR) was used to amplify three overlapping cDNA fragments of the LGT TP21 or LGT E5 genome. The sequences of the PCR primers were derived from the published coding region of LGT TP21 (Iacoco-Connors et al., Virology 188:875–880, 1992; Mandl et al., Virology 185:891–895, 1991). The PCR fragment corresponding to the 5'-noncoding region was generated using a primer which contained the first 21 conserved 5'-terminal nucleotides of the TBEV genome (Dobrikova et al., Bioorg. Chem. 21:528–534, 1995; Mandl et al., Virology 166:197–205, 1988; Mandl et al., J. Virol. 65:4070–4077, 1991). All upstream primers contained a PvuI cleavage site. Each PCR product was cloned in *E. coli* BD1528 using the p5'-2(NotI, XhoI, □HindIII) vector (Cahour et al., Virology 207:68–76, 1995). The complete nucleotide sequence of the TP21 and E5 genomes was determined by sequencing three overlapping cDNA clones on both DNA strands by the dideoxynucleotide chain termination method (Sanger et al, Proc. Natl. Acad. Sci. U.S.A., 74:5463–5467, 1977). Several independent clones for each third of the genome were sequenced.

Sequence analysis revealed that the TP21 or E5 genome was 10, 940 or 10,941 nucleotides in length, respectively, and contained a single open reading frame encoding a 3,414 amino acid polyprotein. The sequence data were used to assess the relationship of LGT TP21 or E5 virus to other members of the flavivirus genus. The overall protein sequence homology between LGT and TBEV Far Eastern subtype (strain Sofjin) was about 84.2%. In contrast, the overall sequence homology between LGT and DEN4, a mosquito-borne flavivirus, was only 39.4%. Among the tick-borne LGT and TBEV flaviviruses, the structural C, preM and E proteins are the least conserved (74%, 75% and 88% homology, respectively), whereas the nonstructural proteins exhibit greater sequence conservation (90–95%).

FIGS. 1A–1B show the 5'- and 3'-noncoding region (NCR) sequences of LGT E5 and TP21 viruses compared to the previously published sequences of Powassan virus, TBEV European subtype (prototype strain Neudoerfl) and Far Eastern subtype (strain Sofjin) viruses. The LGT E5 5'NCR is 130 nucleotides in length and differs from the 5'NCR of TP21 virus by deletion of a G nucleotide at position 61 and by the presence of a C nucleotide instead of a G at position 35. Alignment of the 5'NCR of TBE complex virus genomes shows that two domains between nucleotides 1–30 and 82–129 are conserved in the corresponding regions of TBEV, LGT and Powassan (POW) virus. Sequence between these domains is hypervariable, and the POW and LGT genomes sustained a deletion in this region compared to TBEV strains. Among the tick-borne flaviviruses, the 3' noncoding sequence varies significantly in length: LGT E5 or TP21 contains 566 nucleotides, POW contains 480 nucleotides and TBEV strains contain 350–750 nucleotides.

The alignment of 3'NCRs (FIG. 1B) revealed that the last 95 3'-terminal nucleotides were highly conserved among all sequenced tick-borne flaviviruses. Only four nucleotides in this region distinguish LGT E5 or TP21 virus from TBEV Far Eastern strain. Variation in length of the 3'NCR of tick-borne flaviviruses was observed primarily between the stop codon and the last 325 3'-terminal nucleotides, the latter being a region that exhibits a high degree of sequence conservation. The LGT genome has: (i) a 172 or 80 nucleotide insertion in this region compared to the TBEV Far Eastern strain or POW and (ii) a 182 nucleotide deletion compared to the TBEV European subtype strain. The 3'NCR of LGT E5 strain differed from its LGT TP21 parent by the insertion of a dinucleotide (AC) between positions 10,515 and 10,516 and by deletion of C and U at position 10,599 and 10,633, respectively.

The complete sequence of the LGT TP21 parent was compared to that of its more attenuated LGT E5 derivative in an attempt to identify potential genetic determinants of neuroinvasiveness and neurovirulence. This analysis revealed 24 nucleotide differences, eleven of which resulted in an amino acid substitution in the corresponding polyprotein (Table 2). Amino acid changes were located in the C, E, NS1, NS2A and NS3 proteins. Sequence analysis of separate TP21 cDNA clones which encoded the E protein revealed that a $C_{1436}$>U was present in three of four clones. Interestingly, mutation $Asn_{668}$>Asp in the E protein of strain E5 corresponds to a substitution observed previously in the E protein of a partially attenuated mutant of TBEV (Holzmann et al., J. Virol. 64:5156–5159, 1990; Mandl et al., J. Virol. 63:564–571, 1989). To identify the relative importance of the 11 amino acid differences in the virulence of the LGT TP21 and E5 strains, different combinations of LGT virus genes were introduced into the DEN4 cDNA genome by replacing corresponding DEN4 genes as described below.

TABLE 1A

| Construct | Amino acid/nucleotide sequences | SEQ ID NO. |
|---|---|---|
| pLGT(CME)/DEN4 | | |
| | M A G K G L N S R N T | 14 |
| | AGAGAGCAGATCTCTGGAAAAATGGCCGGGAAG... | |
| | ...GGCTTGAACTCGAGGAACACT | 15 |
| | BglII Xhol | |
| pLGT(ME)/DEN4 | | |
| | I L Q R R G S R R T G L N S R N T | 16 |
| 1. | ATCCTGCAGCGCCGAGGAAGTAGAAGGACG... | |
| | ...GGCTTGAACTCGAGGAACACT | 17 |
| | PstI XhoI | |
| | L N G R K R S I I D G L N S R N T | 18 |

TABLE 1A-continued

| Construct | Amino acid/nucleotide sequences | SEQ ID NO. |
|---|---|---|
| 2. | CTGAACGGGAGAAAAAGATCGATCATTGAC... | |
| | ...GGCTTGAACTCGAGGAACACT | 19 |
| | ClaI XhoI | |
| | L N G R K R S A V D G L N S R N T | 20 |
| 3. | CTGAACGGGAGAAAAAGGTCTGCAGTTGAC... | |
| | ...GGCTTGAACTCGAGGAACACT | 21 |
| | PstI XhoI | |
| | M A F S L V A R E R G L N S R N T | 22 |
| 4. | ATGGCGTTTTCCTTGGTTGCAAGAGAGAGA... | |
| | ...GGCTTGAACTCGAGGAACACT | 23 |
| | BstBI XhoI | |
| pLGT(NS1,2A)/DEN4 | | |
| | G T N S R N P T R G R R S W P L N | 24 |
| | GGCACGAACTCGAGGAACCCAACC... | |
| | ...AGGGGGAGACGATCGTGGCCTCTTAAC | 25 |
| | XhoI PvuI | |
| pLGT(NS1,2A,2B,d3)/DEN4 | | |
| | G T N S R N P T G T G W I R K K R | 26 |
| | GGCACGAACTCGAGGAACCCAACC... | |
| | ...GGCACGGGCTGGATTCGAAAGAAAAGA | 27 |
| | XhoI BstBI | |
| pLGT(NS2B,3)/DEN4 | | |
| | G A S R R S F N E S G R R S I T L | 28 |
| | GGAGCCTCAAGACGATCGTTTAATGAG... | |
| | ...TCTGGAAGAAGATCTATAACTCTC | 29 |
| | PvuI BglII | |

TABLE 1B

| SEQ ID NO: | LGT cDNA | Viability |
|---|---|---|
| 15 | 129–2379 | No |
| 17 | 403–2379 | No |
| 19 | 426–2379 | No |
| 21 | 428–2379 | Yes |
| 23 | 490–2379 | No |
| 25 | 2382–4205 | No |
| 27 | 2382–5161 | No |
| 29 | 4201–6456 | No |

Note: The terminal sequences of the corresponding cDNA fragments of LGT TP21 and LGT E5 are identical. Restriction enzyme-cleaved LGT TP21 or E5 cDNA fragments were inserted into DEN4 cDNA at appropriate sites as indicated by the underlined sequence. The amino acid and the encoding nucleotide sequences of LGT TP21 are in bold letters. Infectivity of RNA transcripts from DNA consructs was tested by transfecting simian or mosquito cells and evaluating cell cultures for evidence of infection by immunofluourescence assay (IFA).

EXAMPLE 3

Construction of LGT/DEN4 Chimeras and Viability Determination

Chimeric LGT/DEN4 viruses were constructed to analyze the genetic basis for reduced neurovirulence, tissue tropism and peripheral invasiveness of Langat virus and to develop a safe and effective live attenuated virus vaccine against the antigenically related TBEV. Full-length DEN4 cDNA was used to engineer chimeric constructs containing the LGT C-preM-E, preM-E, NS1-NS2A, NS1-NS2A-NS2B-dNS3 or NS2B-NS3 genes with the remaining sequences being derived from DEN4 (Table 1A). In each instance, the terminal sequences of the corresponding cDNA fragments of LGT TP21 and LGT E5 used to construct the chimeras were identical.

TABLE 2

| Strain | E5 | | TP21 | |
|---|---|---|---|---|
| Gene | NT, | AA | NT, | AA |
| C | $C_{371}$ | $Pro_{80}$ | A | Thr |
| | $A_{461}$ | $Ile_{110}$ | C | Leu |
| preM | $U_{514}$ | | G | |
| E | $A_{1327}$ | | C | |
| | $A_{1342}$ | | G | |
| | $C_{1436}$ | $Thr_{435}$ | C/U | Thr/Ile |
| | $U_{1567}$ | | A | |
| | $A_{1823}$ | $Ser_{564}$ | G | Gly |
| | $C_{1968}$ | $Ser_{612}$ | U | Phe |
| | $G_{2135}$ | $Asp_{668}$ | A | Asn |
| NSI | $A_{3008}$ | $Met_{960}$ | G | Val |
| | $U_{3403}$ | | C | |
| NS2A | $G_{3635}$ | $Ala_{1168}$ | C | Pro |
| | $C_{3637}$ | | G | |
| | $A_{3964}$ | | G | |
| NS3 | $G_{4662}$ | $Ser_{1510}$ | A | Asn |
| | $A_{5339}$ | $Tyr_{1736}$ | U | Phe |
| | $U_{5374}$ | | C | |
| | $C_{5546}$ | $Leu_{1805}$ | U | Phe |

Note: NT or AA indicates nucleotide or amino acid residue at indicated position of LGT E5 genome or polyprotein. Polyprotein sequence of strain TP21 determined in this study differed from that of the TP21 polyprotein published earlier (Iacoco-Connors et al., Virology 188:875–880, 1992; Mandl et al., Virology 185:891–895, 1991). Glu-152, Ser-564, Ser-612, Met-960, Ala-1168, Ile-2149, Val-2357, Ser-2775, Ala-2921, Cys-3157 and Val-3158 were replaced by Asp, Gly, Phe, Val, Pro, Met, Ile, Cys, Gly, Trp and Leu residues, respectively.

Plasmid DEN4 p2A(XhoI) (Bray et al., Proc. Natl. Acad. Sci. U.S.A. 88:10342–10346, 1991) and pTBEV(ME)/DEN4 (Pletnev et al., Proc. Natl. Acad. Sci. U.S.A. 89:10532–10536, 1992) were used to substitute two or more LGT genes for the corresponding DEN4 genes. Oligonucleotide-directed mutagenesis was performed to introduce a ClaI site instead of the unique Asp718 site at the 3' end of dengue sequence in p2A(XhoI). To facilitate construction of chimeric LGT TP21(CME)/DEN4 or LGT E5(CME)/DEN4 cDNA (Table 1A), the cDNA region encoding the DEN4 C, preM, and E genes, extending from BglII (nucleotide 88) to the XhoI site (nucleotide 2342) was replaced with the corresponding sequence of TP21 or E5 virus. To construct chimeric LGT(ME)/DEN4 cDNA containing the preM and E genes of the Langat wild type TP21 strain or its more attenuated E5 derivative, four different junctions between the DEN4 C gene and LGT preM gene were created in chimeric DNA plasmids (Table 1A). For example, construct number 3 of pLGT(ME)/DEN4 was prepared as follows. The PCR fragment which contains preM-E genes between the introduced PstI site of TP21 at nucleotide 422 or E5 at nucleotide 423 and the XhoI site (TP21 nt 2379 or E5 nt 2380) near the 3' end of the E gene was inserted into the DEN4 vector replacing the corresponding DEN4 sequence, yielding a chimera similar to that containing the preM and E genes of TBEV described previously (Pletnev et al., Proc. Natl. Acad. Sci. U.S.A. 89:10532–10536, 1992). Sequences at the junctions between LGT and DEN4 genes in each chimeric plasmid were verified by sequencing across the regions. Functional integrity of the chimeric viruses was demonstrated by their ability to direct protein synthesis using a rabbit reticulocyte lysate or in a T7-vaccinia virus transient expression system (Elroy-Stein et al., Proc. Natl. Acad. Sci. U.S.A. 86:6126–6130, 1989).

EXAMPLE 4

Growth of Chimeras in Cell Culture

Full-length RNA transcripts made from the chimeric cDNA templates described above were tested for infectivity by transfecting simian $LLCMK_2$, simian Vero and mosquito C6/36 cells in the presence of DOTAP (Pletnev et al., supra.). Nine days after transfection, cells in a 24-well plate were transferred to a 6-well plate and a chamber slide. On day 12 and again on days 16, 20, 24, 28, 32, 36, and 44, cells were split and passaged. In addition, cells were examined on each of these days by immunofluorescence assay (IFA) for the presence of DEN4 and LGT antigens using a 1 :300 dilution of DEN4- or LGT-specific hyperimmune mouse ascitic fluid (HMAf). An infectious virus was only recovered from two of the 16 constructs (8 of LGT TP21/DEN4 and 8 of LGT E5/DEN4) shown in Table 1B and only in mosquito cells. These chimeric viruses are designated: (i) TP21/DEN4 for LGT wild type TP21 strain/DEN4 chimera which contains LGT TP21 preM and E genes; and (ii) E5/DEN4 for LGT attenuated E5 strain/DEN4 chimera which contains LGT E5 preM and E genes. When IFA indicated that 70–100% of cells were infected, cells in the 6-well plate were mixed with a two-fold excess of uninfected cells, and the resulting mixture was inoculated into a 75-$cm^2$ flask which was incubated for 7 days. The infected cells were harvested together with the medium, mixed with an equal volume of fetal bovine serum (FBS), frozen at −70° C. and used later as seed to prepare suspensions of progeny virus. The titer of such virus suspensions was determined by plaque assay on mosquito C6/36 cells.

TP21/DEN4 and E5/DEN4 chimeras were amplified once in mosquito C6/36 cells in a 75-$cm^2$ flask. Viral RNA was then isolated and reverse transcribed with oligo 2634 which is complementary to the DEN4 sequence from nucleotides 5090–5110 (SEQ ID NO: 11). Single-stranded cDNA was used as a PCR template using with the primer pairs oligo 239 (SEQ ID NO: 12) and oligo 444 (SEQ ID NO: 13). The PCR products were digested with HindIII and BamHI and cloned into the pGEM3 vector. Sequence of the LGT/DEN4 junction sites was confirmed by direct analysis of the cloned DNA inserts.

During the initial characterization of the TP21/DEN4 and E5/DEN4 chimeras, sequence analysis confirmed the junction sequences between DEN4 and LGT preM genes or LGT E and DEN4 NS1 genes. Importantly, the chimeras differed in their LGT-derived sequences at only four amino acid positions in the E protein (Table 2). In addition, immunoprecipitation of viral proteins from infected mosquito cell culture indicated that both of these chimeras produced the expected proteins. The LGT preM protein of TP21/DEN4 or E5/DEN4 was sensitive to digestion with endoglycosidase F or H, whereas the E protein was resistant to digestion by these enzymes. This indicated that LGT E protein expressed by either chimera in mosquito cells was not glycosylated despite the presence of a potential glycosylation site in the E sequence.

Figure 2B:
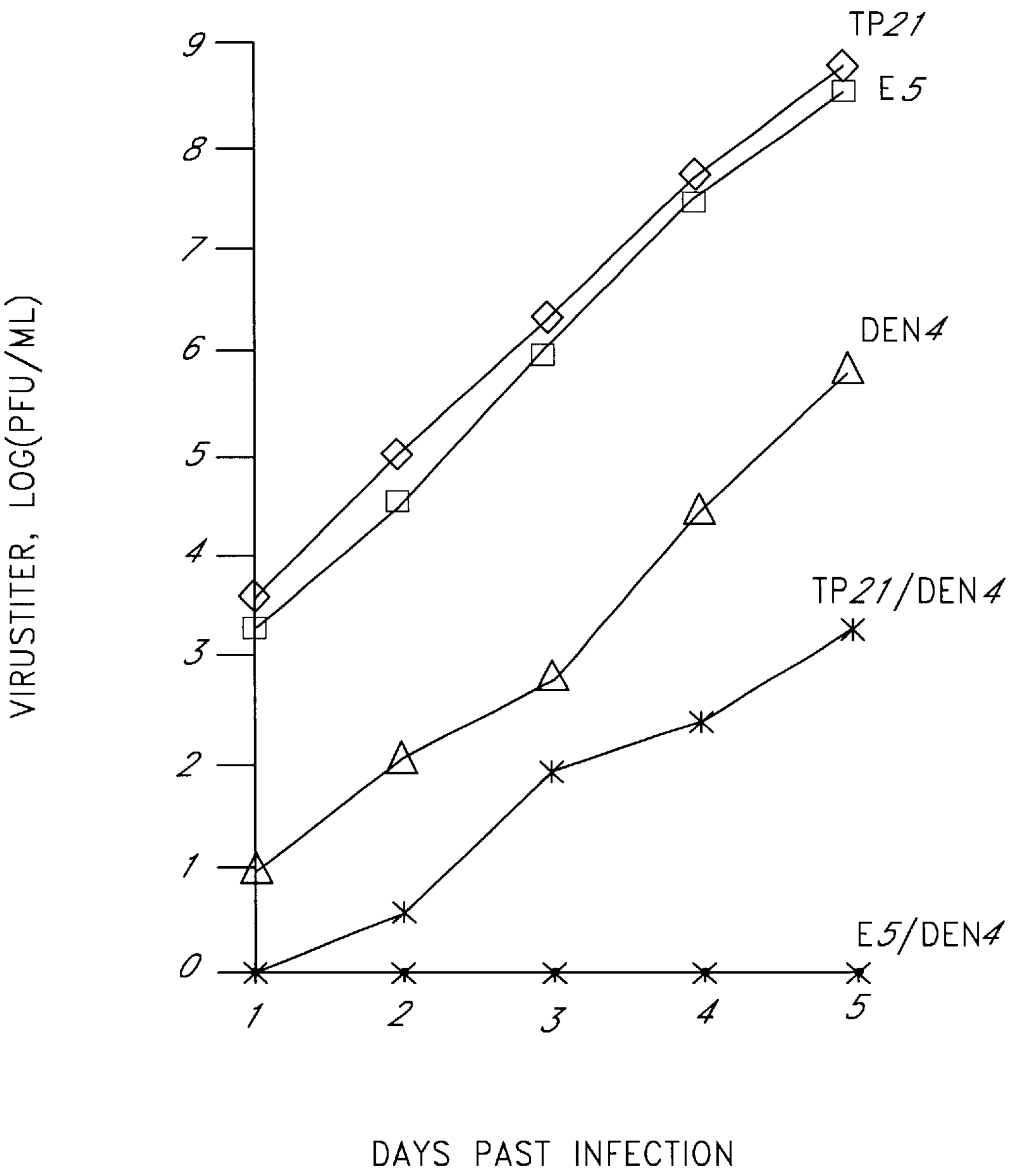
Figure 2C:
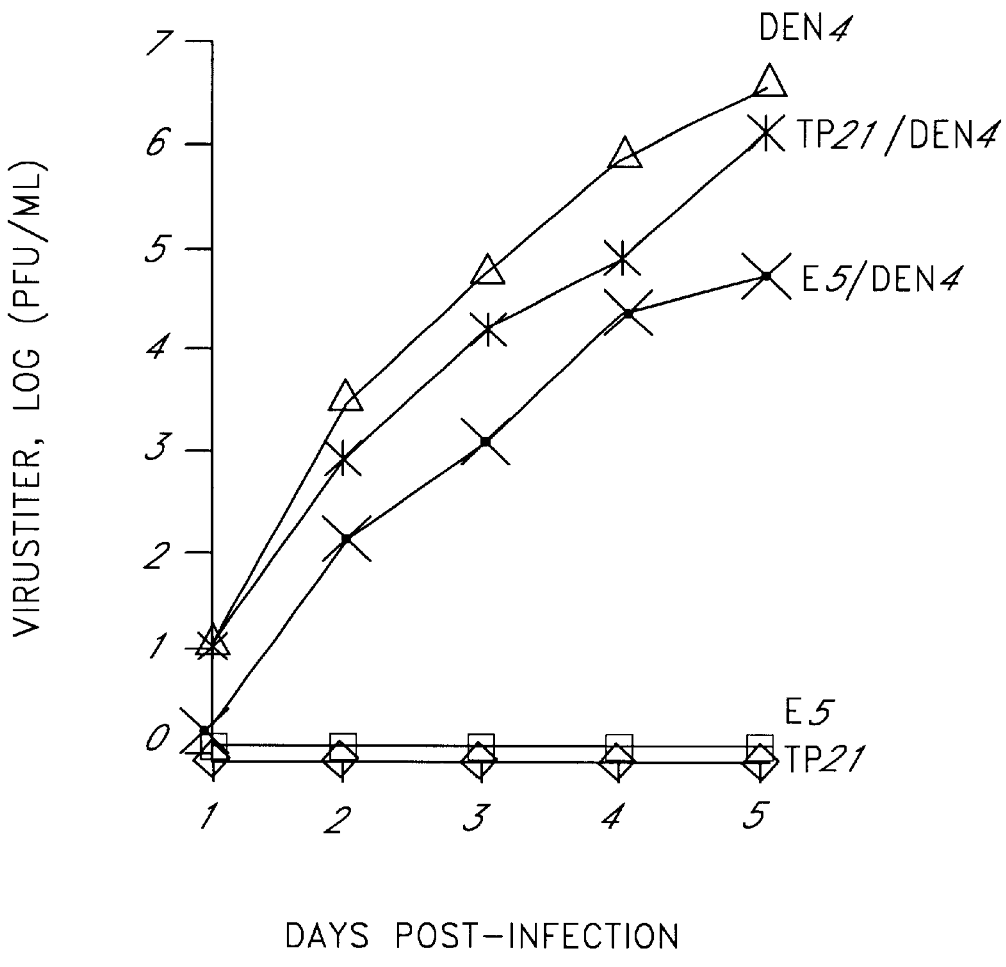

The LGT TP21 and E5/DEN4 chimeras were compared to each other and to their parental viruses with respect to pattern of replication and maximum yield in simian and mosquito cells (FIG. 2). When inoculated at a multiplicity of infection (MOI) of 0.01, the chimeras grew to a moderate titer in mosquito cells, namely $10^{4.8}$ to $10^{6.0}$ PFU/ml. In contrast, the growth of their parent LGT TP21 or E5 virus in mosquito cells was totally restricted when cell culture harvests were assayed by plaque assay on mosquito cells. This restriction was observed even though a MOI of 1,000 was used. Also, viral replication was not detected when less LGT parental virus (ranging from a MOI of 0.01 to 100) was used for inoculation of mosquito cells. In addition, IFA failed to detect evidence of viral replication in any of these instances. The titer attained by the chimeras in mosquito cells on day 5 was 10- to 100-fold reduced compared to DEN4. Unlike DEN4, the two chimeras induced a chronic non-cytopathic infection of mosquito cells. Also, compared to DEN4, the two chimeras produced smaller plaques. Plaque size averaged 5.0 mm for TP21/DEN4,2.0 mm for E5/DEN4 and 11.5 mm for DEN4.

A different hierarchy of viral replication was observed when simian cells were analyzed as cell substrates. Chimerization of LGT TP21 or E5 with DEN4 significantly reduced the efficiency of viral replication in simian cells compared to parental LGT TP21 or E5 virus as well as DEN4. Consequently, the LGT/DEN4 chimeric viruses grown in mosquito cells were unable to produce plaques in simian cells. In addition, these chimeras did not replicate efficiently in simian cells as indicated by plaque assay of growth yield in mosquito cells. In contrast, parental LGT TP21 or E5 was able to produce plaques with high efficiency and grow to high titer in simian cells, i.e. approximately $10^8$ to $10^9$ PFU/ml, a level greater than that achieved by DEN4.

Simian cells were not completely refractory to the chimeric viruses because virus propagated in permissive mosquito cell culture did initiate slow and partially restricted viral replication in simian $LLCMK_2$ or Vero cells inoculated at a MOI of 0.5. In addition, spread of virus in these cell cultures differed from that of parental LGT TP21 or E5 virus that were cytopathic and attained a high titer by day 5 when inoculated at a MOI of 0.01. In contrast, infection of simian cells with either chimera at a MOI of 0.5 did not produce cytopathic effects and progressed very slowly as monitored by IFA. An incubation period of 24 to 48 days was required for 80–100% of simian cells to become infected. At this time, a chronic infection without cytopathic effect became established and such chronically infected cells could be maintained during incubation and subculture for 10 months without apparent visible effect. Virus yield from these simian cell cultures at the time of maximum infection was measured by plaque assay on mosquito cells and found to be reduced by 90% from the level attained when either chimeric virus was grown in mosquito cells. The yield of either chimeric virus from infected simian $LLCMK_2$ cells did not produce plaques on these cells. This was also the case for the LGT E5/DEN4 chimera grown in simian Vero cells. In contrast, a reduced number of very small faint plaques was produced by the LGT TP21/DEN4 chimera in these cells, a finding consistent with the limited replication of the chimera in simian cells. When chimeric TP21/DEN4 or E5/DEN4 virus harvested from simian cells chronically infected for 8 months was passaged in mosquito cell culture and attained a high titer, the virus yield retained its restriction of growth and plaque formation in simian cells.

These results indicate that chimerization of LGT TP21 or LGT E5 with DEN4 significantly reduced the replicative capacity of there chimeras in simian cells compared to either parental virus. This is in contrast to previous results showing that the chimera TBEV(ME)/DEN4 replicated 1,000 times more efficiently in simian cells than did DEN4 (Pletnev et al., supra.).

The neurovirulence and neuroinvasiveness of TP21, E5 or LGT/DEN 4 chimeric virus was studied in an in vivo mouse model as described in Examples 5 and 6 below.

EXAMPLE 5

Neurovirulence Studies

The neurovirulence of LGT TP21, LGT E5, DEN4 and chimeric TP21/DEN4 or E5/DEN4 viruses was evaluated in 3-day-old outbred Swiss mice. Groups of 10 to 14 mice were inoculated intracerebrally (IC) with decimal dilutions of virus ranging from $10^{-2}$ to $10^{7}$ PFU in 20 $\mu$l modified Eagle's medium (MEM) containing 0.25% human serum albumin. Mice were observed for 28 days for non-fatal or fatal encephalitis.

Wild type LGT TP21 was highly neurovirulent as shown by its $LD_{50}$ of 0.4 PFU in suckling mice, i.e. one PFU was lethal for suckling mice (Table 3). Neurovirulence of the more attenuated LGT strain E5 by the same route was 50 times less. DEN4 was even less neurovirulent, as disease or death was observed only when suckling mice were inoculated with a high dose. Intracerebral $LD_{50}$ of DEN4 was estimated to be 8,000 PFU. Chimeric TP21/DEN4 or E5/DEN4 exhibited a significant reduction in neurovirulence compared to its LGT parent when tested by direct inoculation into the brain of suckling mice. Thus, the intracerebral $LD_{50}$ of TP21/DEN4 was 2,500 PFU which was about 6,250 fold less than its LGT TP21 parent (0.4 PFU). E5/DEN4 was even more attenuated, having an IC $LD_{50}>10^{5}$ PFU. In addition, E5/DEN4 was 44 times less neurovirulent than TP21/DEN4. Thus, the TP21/DEN4 or E5/DEN4 chimeric virus retained the low mouse neurovirulence of its DEN4 parent rather than the higher mouse neurovirulence of its Langat virus parent. Likewise, the LGT/DEN4 chimeras were at least 6,250 times less neurovirulent in mice than their parental LGT TP21 or E5. This significant reduction of neurovirulence appeared to correlate with the restricted growth of these chimeras in simian cells.

Surprisingly, there was a dramatic reduction in neurovirulence of the LGT TP21(ME)/DEN4 and LGT E5(ME)/DEN4 chimeras compared to the TBEV(ME)/DEN4 (Table 3). The TP21/DEN4 and E5/DEN4 chimeras were 125 and 5500 times less neurovirulent, respectively, than the TBEV chimera.

TABLE 3

| | $LD_{50}$ (PFU) in Mice | | | | |
|---|---|---|---|---|---|
| | Immunocompetent | | | | |
| Virus | Intracerebral | Fold-reduction vs. TBEV | Intraperitoneal | Fold-reduction vs. TBEV | SCID Intraperitoneal |
| DEN4 | $8 \times 10^{3}$ | $8 \times 10^{4}$ | $>10^{7}$ | $>7.1 \times 10^{5}$ | $>10^{7}$ |
| TBEV | $10^{-1}$ | — | $1.4 \times 10^{1}$ | — | NT |
| TBEV (ME)/DEN4 | $2 \times 10^{1}$ | 200 | $>10^{7}$ | $>7.1 \times 10^{5}$ | NT |
| LGT TP21 | $4 \times 10^{-1}$ | 4 | $5 \times 10^{3}$ | 357 | $4 \times 10^{-3}$ |
| LGT TP21/DEN4 | $2.5 \times 10^{3}$ | $2.5 \times 10^{4}$ | $>10^{5}$ | $>7.1 \times 10^{3}$ | $>10^{7}$ |
| LGT E5 | $2 \times 10^{1}$ | 200 | $>10^{7}$ | $>7.1 \times 10^{5}$ | $6 \times 10^{-2}$ |
| LGT E5/DEN4 | $1.1 \times 10^{5}$ | $1.1 \times 10^{6}$ | $>10^{5}$ | $>7.1 \times 10^{3}$ | $>10^{7}$ |

50% lethal dose of virus ($LD_{50}$) was estimated by intracerebral inoculation of 3-day-old Swiss mice or by intraperitoneal inoculation of 3-week-old Swiss or SCID mice with decimal dilutions of virus. $LD_{50}$ of TP21 or E5 virus is expressed as PFU measured in Vero cells and $LD_{50}$ of DEN4, TP21/DEN4 or E5/DEN4 virus is expressed as PFU measured in C6/36 cells. $LD_{50}$ of TBEV and TBEV(ME/DEN4 was determined previously and presented here for purpose of comparison (Pletnev et al., Proc, Natl. Acad. Sci. U.S.A. 89:10532–10536, 1992; Pletnev et al., J. Virol. 67:4956–4963, 1993). NT, Not tested.

EXAMPLE 6

Neuroinvasiveness Studies

Neuroinvasiveness (peripheral neurovirulence) of parental or chimeric viruses was evaluated in 3-week-old female Swiss mice that were inoculated intraperitoneally (IP) in groups of ten with: (i) 10, $10^2$, $10^3$, $10^4$, $10^5$, $10^6$ or $10^7$ PFU of LGT TP21 or LGT E5 virus; or (ii) $10^5$ PFU of TP21/DEN4, E5/DEN4 or DEN4 virus. Mice were observed for 21 days and surviving mice were bled to evaluate antibody response. Surviving mice were challenged IP on the next day with 100 or 1,000 IP $LD_{50}$ of parental TP21 virus and observed for an additional four weeks.

LGT TP21 was also moderately virulent for 3-week-old mice when inoculated by a peripheral route. The IP $LD_{50}$ was approximately $5\times10^3$ PFU. In contrast, chimeric TP21/DEN4 exhibited lower peripheral neuroinvasiveness for adult mice with an IP $LD_{50}$ of $>10^5$ PFU. The attenuated LGT E5 strain exhibited much lower peripheral virulence than its LGT TP21 parent. Only 10–20% of adult mice inoculated IP with $10^7$ PFU of LGT E5 showed symptoms of encephalitis which made it difficult to detect an effect of chimerization on neuroinvasiveness. However, the data regarding LGT TP21/DEN4 indicates that chimerization of LGT TP21 with DEN4 reduced or eliminated neuroinvasiveness of LGT for mice.

A more sensitive assay for neuroinvasiveness involved inoculation of immunodeficient (SCID) mice. Although SCID mice lack mature B and T lymphocytes, they do have normal innate immune functions, including functional macrophages, normal to elevated NK cell functions and elevated hemolytic complement activity. In this assay, female 3-week-old CB-17 ICR/scid/scid mice (Bosma et al., Nature 301:527–530, 1983) in groups of 5 were inoculated IP with: (i) $10^5$ or $10^7$ PFU of DEN4, TP21/DEN4 or E5/DEN4 virus or (ii) decimal dilutions of LGT TP21 or LGT E5 ranging from $10^{-4}$ to $10^7$ PFU. These mice were then observed for mortality for 6 weeks.

The ability of immunodeficient SCID mice to detect neuroinvasiveness of TP21 or E5 was approximately $10^{6.3}$ to $10^{8.8}$ greater than was observed for immunocompetent Swiss mice (Table 3). A markedly increased susceptibility to fatal disease was noted when SCID mice were inoculated IP with either of the parental LGT viruses. The $LD_{50}$ of LGT TP21 for immunodeficient mice by the IP route was 0.004 PFU (Table 3). In addition, LGT E5 was also highly virulent for SCID mice by the IP route with a $LD_{50}$ of 0.06 PFU. The incubation period until encephalitis was 12 days and death occurred within the next 5 days. Like parental DEN4 virus, both LGT chimeric viruses lacked detectable neuroinvasiveness for SCID mice. Mice inoculated IP with $10^7$ PFU remained healthy during the 6 week post-inoculation observation interval. These findings indicate that the chimeric TP21/DEN4 or E5/DEN4 had completely lost the neuroinvasiveness of its LGT parent for SCID mice.

The parental TP21 virus itself or its attenuated derivative strain E5 may not be suitable for us in humans as a live-attenuated vaccine against the TBE complex of viruses. The occurrence of vaccine-associated encephalitis, albeit at a very low frequency ($10^{-4.3}$), which was observed during a large clinical trial of the most attenuated vaccine candidate (Yelantsev virus) against TBEV, supports this view (Iacoco-Connors et al., Virology 188:875–880, 1992; Smorodincev et al., in Tick-borne Encephalitis and its Vaccine Prophylaxis, Leningrad, 1986). Live attenuated tick-borne flaviviruses should be free of such a very low level of virulence if possible. In contrast to parental LGT viruses, evaluation of TP21/DEN4 and E5/DEN4 chimeric viruses in the SCID mouse model indicated that the two chimeras were completely avirulent and free of any evidence of neuroinvasiveness in this very sensitive assay system, as a large dose ($10^7$ PFU) of either chimeric virus failed to invade the CNS and cause encephalitis or death following inoculation at a peripheral site. This suggests that proteins encoded by regions of the LGT genome other than the preM and E genes are required for either LGT virus to spread from a peripheral site to the brain and cause encephalitis.

Neuroinvasiveness could be differentiated from neurovirulence. Thus, LGT E5 exhibited moderate neurovirulence when virus was inoculated directly into the brain of suckling mice ($LD_{50}$ of 20 PFU) whereas its $LD_{50}$ when inoculated IP was $>10^7$ PFU. Clearly, neurovirulence is required for LGT to produce encephalitis when inoculated by a peripheral route such as IP inoculation. However, other properties of these flaviviruses are required for virus to disseminate to the brain.

EXAMPLE 7

Immunogenicity and Protective Efficacy of LGT/DEN4 Chimeric Viruses Against Langat Virus Challenge Mice were used to determine the immunogenicity and protective efficacy of the LGT/DEN4 chimeras. Mice inoculated IP with $10^2$ PFU of TP21 or E5, or of $10^5$ PFU of TP21/DEN4 or E5/DEN4, developed a high antibody response to TP21 virions as measured by enzyme linked immunosorbent assay (ELISA; Table 4). In addition, these mice developed a high level of neutralizing antibodies against LGT TP21 as measured by plaque reduction. In contrast, mice inoculated IP with $10^5$ PFU of DEN4 failed to develop TP21 or E5 neutralizing antibodies measurable by ELISA.

TABLE 4

| Virus | Dose for immu-Nization (PFU) | Mean of antibody titer (reciprocal) measured by ELISA[1] | NT-test[2] |
|---|---|---|---|
| DEN4 | $10^5$ | <50 | <20 |
| TP21 | $10^2$ | 7560 | 703 |
| E5 | $10^2$ | 7080 | 761 |
| TP21/DEN4 | $10^5$ | 2400 | 288 |
| E5/DEN4 | $10^5$ | 2320 | 327 |

[1]Antibody titer in mouse serum collected three weeks after intraperitoneal immunization was determined using purified TP21 virions as antigen.
[2]Neutralizing antibodies were measured by a 50% plaque reduction neutralization test using TP21 virus.

Twenty-three days after inoculation with TP21/DEN4, E5/DEN4, TP21 or E5, mice were challenged IP with 100 or 1,000 IP $LD_{50}$ of TP21 (Table 5). All of the mice that had been immunized previously with TP21/DEN4 or E5/DEN4 developed a high titer of neutralizing antibodies and were completely protected against IP challenge of TP21. In contrast, mice immunized IP with DEN4 were only partially protected: three of ten mice died when challenged with 100 IP $LD_{50}$ of LGT TP 21. Each of the 30 nonimmunized control mice developed encephalitis and 25 subsequently died. As observed earlier, these results indicate that an immune response to DEN4 nonstructural proteins was not able to provide complete protection for mice against LGT TP21.

TABLE 5

| Infecting virus | | Mortality following | Mortality of survivors following inoculation IP with TP21 | |
|---|---|---|---|---|
| | Dose | intraperitoneal | (Intraperitoneal $LD_{50}$) | |
| Strain | (PFU) | inoculation | 100 | 1000 |
| TP21 | $10^2$ | 1/10 | 0/9 | |
| E5 | $10^2$ | 0/10 | 0/10 | |
| | $10^7$ | 1/10 | | 0/9 |
| DEN4 | $10^5$ | 0/10 | 3/10 | |
| TP21/DEN4 | $10^5$ | 0/40 | 1#/10 | 0/30 |
| E5/DEN4 | $10^5$ | 0/40 | 0/10 | 0/30 |
| Non-infected controls | NA | 0/30 | 8/10* | 17/20* |

*Mice that survived intraperitoneal challenge with TP21 were paralyzed for 3–5 days.
Traumatic death.

In a subsequent study (Table 6), each of 5 mice inoculated with $10^5$ PFU of DEN4 failed to resist challenge with 1,000 IP $LD_{50}$ of LGT TP21, whereas each of five mice immunized IP with $10^5$ PFU of chimeric TP21/DEN4 or E5/DEN4 survived the same challenge with LGT TP21. Thus, the LGT E and preM proteins appear to represent the major protective antigens of the chimeras responsible for complete resistance to lethal LGT challenge.

TABLE 6

| Immunizing virus | Dose of immu-Nization (PFU) | ELISA Mean antibody titer | Mean neut. antibody titer | Mortality following challenge IP with 1000 intraperitoneal $LD_{50}$ of TP21 |
|---|---|---|---|---|
| E5/DEN4 | 10 | 240 | 52 | 0/5 |
| | $10^3$ | 200 | 52 | 1/5 |
| | $10^5$ | 1530 | 151 | 0/5 |
| E5/DEN4-UV | 10* | <100 | <20 | 4/5 |
| | $10^3$* | <100 | <20 | 4/5 |
| | $10^5$* | 100 | <20 | 4/5 |
| TP21/DEN4 | 10 | 240 | 65 | 1/5 |
| | $10^3$ | 280 | 174 | 0/5 |
| | $10^5$ | 3680 | 257 | 0/5 |
| TP21/DEN4-UV | 10* | <100 | <20 | 5/5 |
| | $10^3$* | <100 | <20 | 5/5 |
| | $10^5$* | <100 | <20 | 3/5 |
| TP21 | 10 | 6400 | 528 | 0/2 |
| E5 | 10 | 6400 | 536 | 0/3 |
| DEN4 | $10^5$ | <100 | <20 | 5/5 |
| Control | NA | <100 | <20 | 5/5 |

*Titer prior to UV irradiation that completely inactivated infectivity.

It is possible that the immunogenicity and protective efficacy of the parental LGT viruses and their DEN4 chimeras resulted from immunization with pre-formed antigens present in viral preparations inoculated IP and not from antigens produced by virus that replicated in vivo. This issue was addressed by evaluating antibody responses and protective efficacy of virus preparations that contained only 10 PFU. In addition, the chimeras were evaluated at two other levels of infectivity, namely $10^3$ or $10^5$ PFU (Table 6). At each of the three doses evaluated, virus was tested without modification or after complete inactivation by UV irradiation. Prior to performing this study, the time required for complete inactivation of infectivity by UV was determined by kinetic analysis to be 60 minutes.

Mice were observed for 21 days, and survivors were bled 22 days after inoculation to evaluate antibody response measured by ELISA or a plaque-reduction neutralization test. Surviving mice were challenged IP at 24 days with 1,000 IP $LD_{50}$ ($5\times10^7$ PFU) of LGT TP21 and observed for the next four weeks.

As little as 10 PFU of either chimera regularly induced neutralizing and ELISA antibodies at a titer of 1:50 or higher (Table 6), whereas only 1 of 10 mice that received UV-inactivated $10^5$ PFU of a chimera developed a low level of ELISA antibodies and none developed measurable neutralizing antibodies. The response of these mice challenged with TP21 (1,000 IP $LD_{50}$) was consistent with the immunological response. Only 1 of 10 mice inoculated IP with 10 PFU of a chimera succumbed to challenge, whereas 7 of 10 mice that received UV-inactivated $10^5$ PFU died after challenge. it appears that successful immunization by the two chimeras primarily reflects the effect of viral replication and not the effect of a large mass of pre-formed viral antigens.

EXAMPLE 8

Immunogenicity and Protective Efficacy of LGT/DEN4 Chimeric Viruses Against TBEV Challenge Mice are used to determine the immunogenicity and protective efficacy of the LGT/DEN4 chimeras. Twenty-three days after inoculation with TP21/DEN4, E5/DEN4, or DEN4, mice are challenged with $10^3$ or $10^5$ PFU of TBEV or one of its highly virulent tick-borne flavivirus relatives, such as Omsk hemorrhagic fever virus, Kyasamur forest disease virus, Negishi virus, Powassan virus, or Central European tick-borne encephalitis virus. All of the mice immunized previously with TP21/DEN4 or E5/DEN4 develop a high titer of neutralizing antibodies and are completely protected against IP challenge of TBEV. In contrast, mice immunized IP with DEN4 are only partially protected or not protected at all. Each of the nonimmunized control mice develope encephalitis and die. These results indicate that an immune response to DEN4 nonstructural proteins is not able to provide complete protection for mice against TBEV or its highly virulent relatives.

In an additional study, each of a group of mice are inoculated with $10^5$ PFU of DEN4 fail to resist challenge with TBEV, whereas each of a group of mice immunized IP with $10^5$ PFU of chimeric TP21/DEN4 or E5/DEN4 survive the same challenge with TBEV. Thus, the LGT preM and E proteins appear to represent the major protective antigens of the chimeras responsible for complete resistance to lethal TBEV challenge.

It is possible that the immunogenicity and protective efficacy of the parental LGT viruses and their DEN4 chimeras results from immunization with pre-formed antigens present in viral preparations inoculated IP and not from antigens produced by virus that replicates in vivo. This issue is addressed by evaluating antibody responses and protective efficacy of virus preparations that contain only limited amounts of virus. In addition, the chimeras are evaluated at two other levels of infectivity, namely $10^3$ or $10^5$ PFU. At each of the three doses, the viruses are tested without modification or after complete inactivation by UV irradiation. Prior to performing this study, the time required for complete inactivation of infectivity by UV is determined by kinetic analysis to be 60 minutes.

Mice are observed for 21 days, and survivors are bled 22 days after inoculation to evaluate antibody response measured by ELISA or a plaque-reduction neutralization test. Surviving mice are challenged IP at 24 days with 1,000 IP $LD_{50}$ of TBEV and observed for the next four weeks.

As little as 10 PFU of either chimera regularly induces neutralizing and ELISA antibodies at a titer of 1:50 or higher (Table 6), whereas only a small percentage of mice that receive UV-inactivated $10^5$ PFU of a chimera develop a low level of ELISA antibodies and none develop measurable neutralizing antibodies. The response of these mice challenged with TP21 (1,000 IP $LD_{50}$) is consistent with the immunological response. Only a small percentage of mice inoculated IP with 10 PFU of a chimera succumb to challenge, whereas a majority of the mice that receive UV-inactivated $10^5$ PFU die after challenge. It appears that successful immunization by the two chimeras primarily reflects the effect of viral replication and not the effect of a large mass of pre-formed viral antigens.

EXAMPLE 9

Testing of Chimeric Flavivirus Vaccines in Primates

Intranasal infection of monkeys represents an infected under natural conditions experimental system in which to test and predict the efficacy of a TBE vaccine for use in humans. Hambleton, P., et al., Infect. Immun., 40:995–1003 (1983). This report showed that the response of rhesus monkeys to intranasal TBE infection is similar to that of humans except that no pyrexia was not observed. The objectives of the present study concerning vaccination against TBE infection in monkeys are: (1) to evaluate the immunogenicity of various candidate chimeric recombinant flavivirus virus vaccines; and (2) to evaluate the protective efficacy of the above-mentioned vaccines against challenge by virulent strains of TBEV or its closely related viruses.

A group of adult rhesus monkeys (Macaca mulatta) of both sexes, weighing 1.8 to 5.1 kg, is used in the study. The animals are housed and fed according to standard protocols well known and accepted in the art. For infection and all sampling procedures, the animals are anesthetized by intramuscular injection with a suitable agent well known in the art, such as ketamine hydrochloride (Vetalar; Parke, Davis & Co.).

The virus strains that are used to infect the test animals are of a clinically important member of the tick-borne encephalitis complex. For example, the Russian spring-summer encephalitis (Far Eastern), Central European encephalitis (Western), Omsk hemorrhagic fever, louping ill, Kyasanur forest disease, Negishi, or Powassan viruses may be used to test the efficacy of the vaccines of the present invention.

The group of monkeys chosen for the study are divided randomly into an experimental group and a control group. The experimental group of monkeys are vaccinated with an effective dose of a chimeric flavivirus vaccine of the present invention, while the control group of monkeys remain untreated. All monkeys are infected with $3\times10^8$ to $5\times10^8$ PFU of a standardized challenge stock of the chosen TBEV. The subject animals are infected intranasally so as to produce clinical results similar to those observed in humans infected with TBEV under natural conditions.

Blood (10 ml) is removed from the subject monkeys for testing at intervals after infection using standard techniques well known in the art. These blood samples are fractionated into their component portions, and the filtered serum samples are stored at −20° C. according to acceptable procedures known in the art. Cerebrospinal fluid (CSF) is taken from monkeys by cisternal puncture, or by other acceptable methods, before infection and 9 to 11 days postinfection. These samples are filtered and stored at −20° C. according to acceptable procedures known in the art. Portions of the unfiltered CSF are examined micorscopically for the presence of leukocytes.

Monkeys are killed at intervals from 4 days to 14 weeks after infection and in extremis by i.v. injection of sodium pentobarbital. Necropsy is carried out immediately. The brain and spinal cord are removed, and portions of tissue from each region are taken for the purpose of virus isolation. The remainder of the central nervous system (CNS) is fixed in buffered 10% neutral Formalin, as are portions of liver, spleen, lung, kidney, and small intestine. After processing by standard methods and embedding in paraffin wax, sections of all the tissues are cut and stained by hematoxylin and eosin. Selected sections of the CNS are also be stained by phosphotungstic acid hematoxylin, by luxol fast blue-cresyl violet, and by the Glees and Marsland modification of the Bielschowsky technique for neurones.

In a majority of the control monkeys infected intranasally with challenge TBEV, there is an onset of clinical neurological signs between 10 and 15 days. These signs consist of tremors of the arms, neck twisting, uncoordination, posterior paresis, and, occasionally, convulsions. These symptoms progress to coma and death 12 to 24 hours after the first onset.

A clinical chemistry examination of the blood and CSF indicates the changes in the subject animals are a result of challenge with TBEV and also provide a means to compare animal and human data. Concerning the blood: changes in the activities of some blood components such as certain serum enzymes are apparent from about 10 days after infection. Asparatate aminotransferase (ASAT) activity may increase. Dehydrogenase and creatine kinase activities may also increase. In contrast, alkaline phosphatase activity may decrease progressively in relation to preinfection levels. Concerning the CSF: the activity of ASAT may be significantly elevated postinfection, however, increases in leukocyte numbers may fail to increase as a result of infection.

Other effects of viral challenge are also observed. Lesions are found in those challenged animals that show clinical signs of disease. These lesions are present principally in the cerebellum, posterior brain stem, and vervical spinal cord, but milder lesions may be present in the cerebral cortex and midbrain. Virus may also appear transiently in the blood of challenged animals. An antibody response by animals challenged with TBEV intranasally may not necessarily be observed.

In contrast to the control group, the experimental group of monkeys remain substantially free of disease symptoms caused by the challenging TBEV. The protection conferred by the chimeric flavivirus vaccine to the experimental group of monkeys demonstrates the safety and efficacy of the chimeric flaviviruses of the present invention.

EXAMPLE 10

A Randomized Trial of LGT/DEN4 Chimeric Virus Vaccine

A LGT/DEN4 chimeric virus vaccine produced as described in the Examples above is used to test the safety and efficacy of such vaccines for human use. This Example is based upon: the study reported by Harabacz, I., et al. Vaccine, 10(3):145–150 (1992). One dose of the virus in the vaccine contains 1.0, 1.5 and 2.0 $\mu$g of recombinant virus particles. The trial is designed as a prospective, multicenter, controlled, double-blind study. Randomization of the participants is performed with regard to dose and vaccination schedule. The three dosages are randomly assigned in a ratio of 1:1:1. Random allocation to the conventional or abbreviated schedule is in a ratio of 2:1. The study centers may be located in various European countries where TBE is known to occur, such as Germany, Yugoslavia, Czechoslovakia and Switzerland.

A group of health adults regardless of sex are enrolled in the study. The age of the participants may range from 18 to 70 years of age. Age and sex are distributed in a balanced fashion between the groups. All volunteers are required to give their informed consent before entering the trial; the study is approved by the appropriate ethical oversight committees at the centers where the studies are performed.

Concerning the schedules of vaccination and observation: the 'conventional' immunization schedule consists of vaccinations on days 0, 28, and 300. Blood sampling for antibody assays occurs on days 0, 28, 42, 56, 300, 314, and 328. The 'abbreviated' immunization schedule consists of vaccination on days 0, 7, and 21. Blood samples are collected on days 0, 21, 28, 35, 49, and 321. The vaccine tested is injected intramuscularly into the deltoid muscle. Each subject is followed up for 28 days after each immunization to monitor for adverse vaccine events.

Antibody assays using standard immunological techniques such as the enzyme-linked immunosorbent assay (ELISA), the hemagglutination-inhibition test (HIT) and neutralization test (NT) are performed. These assays are performed according to methods well known in the art, for example, the HIT may be performed according to the method of Clarke and Casals, Am. J. Trop. Med. Hyg., 7:561–573 (1958), the ELISA according to Heinz, et al., Virology, 126:525–538 (1983), and the NT as described by Klockmann, et al., J. Biol. Stand., 17:331–342 (1989). In NT, the $ND_{50}$ per 0.1 ml may be determined using a virus dose of 100 $TCID_{50}$ per 0.1 ml. Lower limits for seroconversion may be defined as 8 in HIT, 2 I NT, and 160 in ELISA.

The results of the study show that the chimeric flavivirus vaccines of the present invention are safe for use in humans. They also show that immunized individuals seroconvert and produce antibodies against the chimeric flavivirus vaccines. These antibodies have HIT and NT results that indicate that the immune response elicited by the vaccines is protective against TBEV challenge. This study also shows that adverse events related to vaccination are few compared to the well tolerated reactions of a majority of immunized subjects in the study.

The above description of the invention is set forth solely to assist in understanding the invention. It is to be understood that variations of the invention, including all equivalents now known or later developed, are to be considered as falling within the scope of the invention, which is limited only by the following claims.

What is claimed is:

1. A viable chimeric recombinant flavivirus, comprising:

a first region of nucleic acid operably encoding preM and E structural proteins of a Langat virus operably linked to a second region of nucleic acid operably encoding non-structural proteins of a dengue 1 virus, dengue 2 virus, dengue 3 virus, or dengue 4 virus, wherein said Langat virus is defined as an attenuated tick-borne encephalitis virus.

2. The recombinant flavivirus of claim 1, wherein said Langat virus is Langat strain TP21 or Langat strain B5.

3. The recombinant flavivirus of claim 1, wherein said first region of nucleic acid also operably encodes capsid protein from said dengue 1 virus, dengue 2 virus, dengue 3 virus, or dengue 4 virus.

4. The recombinant flavivirus of claim 1, further comprising at least one mutation that does not cause neurovirulence or neuroinvasiveness.

5. An immunogenic composition for generating an immune response against tick-borne encephalitis virus or one of its highly virulent tick-borne flavivirus relatives comprising the chimeric viable recombinant flavivirus of claim 1 in a pharmaceutically acceptable carrier.

6. A recombinant DNA construct comprising: a first region of nucleic acid operably encoding preM and E structural proteins of a Langat virus operably linked to a second region of nucleic acid operably encoding non-structural proteins of a dengue 1 virus, dengue 2 virus, dengue 3 virus, or dengue 4 virus incorporated within an expression vector, wherein said Langat virus is defined as an attenuated tick-borne encephalitis virus.

7. The recombinant DNA construct of claim 6, wherein said vector is a plasmid.

8. A host cell stably transformed with the recombinant DNA construct of claim 5, in a manner allowing expression of said DNA construct.

9. The host cell of claim 8, wherein said host cell is a prokaryotic cell.

10. The immunogenic composition of claim 5, wherein said tick-borne encephalitis virus or one of its highly virulent tick-borne flavivirus relatives is the Eastern or Western subtype or Omsk hemorrhagic fever, louping ill, Kyasanur forest disease, Negishi, or Powassan virus.

* * * * *